United States Patent
Lomicka et al.

(10) Patent No.: US 9,149,345 B2
(45) Date of Patent: *Oct. 6, 2015

(54) MULTIPLE ROOT IMPLANT

(75) Inventors: Matthew Lomicka, Vista, CA (US); Srilakshmi Vishnubhotla, San Diego, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 477 days.

This patent is subject to a terminal disclaimer.

(21) Appl. No.: 12/167,032

(22) Filed: Jul. 2, 2008

(65) Prior Publication Data
US 2009/0061387 A1  Mar. 5, 2009

Related U.S. Application Data

(63) Continuation-in-part of application No. 11/847,476, filed on Aug. 30, 2007, now Pat. No. 8,814,567.

(51) Int. Cl.
*A61C 8/00* (2006.01)
*A61C 8/02* (2006.01)
*A61F 2/30* (2006.01)

(52) U.S. Cl.
CPC ............. *A61C 8/0012* (2013.01); *A61C 8/0018* (2013.01); *A61C 8/0043* (2013.01); *A61C 8/0089* (2013.01); *A61C 8/0006* (2013.01); *A61C 8/0013* (2013.01); *A61F 2002/30436* (2013.01); *A61F 2220/0041* (2013.01)

(58) Field of Classification Search
USPC ................ 433/172–176, 220, 221, 201.1; 623/16.11, 17.17, 23.44, 17.18
See application file for complete search history.

(56) References Cited

U.S. PATENT DOCUMENTS

| | | | |
|---|---|---|---|
| 1,929,425 A | 10/1933 | Hermann | |
| 2,506,845 A | 5/1950 | Randolph | |
| 2,721,387 A | 10/1955 | Ashuckian | |
| 2,857,670 A | 10/1958 | Kiernan, Jr. | |
| 3,314,420 A | 4/1967 | Smith et al. | |
| 3,423,830 A | 1/1969 | Halpern et al. | |
| 3,423,831 A | 1/1969 | Semmelman | |
| 3,497,953 A | 3/1970 | Weissman | |
| 3,628,248 A * | 12/1971 | Kroder et al. | ............... 433/175 |
| 3,685,115 A | 8/1972 | Scott | |

(Continued)

FOREIGN PATENT DOCUMENTS

| | | |
|---|---|---|
| AU | 2006284874 B2 | 3/2012 |
| CA | 2506845 | 7/2004 |

(Continued)

OTHER PUBLICATIONS

International Search Report from related PCT/US08/74645, dated Dec. 29, 2008, 9 pages.

(Continued)

*Primary Examiner* — Yogesh Patel
(74) *Attorney, Agent, or Firm* — Schwegman Lundberg & Woessner, P.A.

(57) ABSTRACT

A dental implant has a body and a plurality of distinct roots that extend outwardly from the main portion that generally define a coronal-apical axis. A porous tantalum metal portion is disposed at the body for engaging bone and the plurality of distinct roots are configured to resist a torsional force that is applied to the dental implant and around the coronal-apical axis.

17 Claims, 8 Drawing Sheets

(56) References Cited

U.S. PATENT DOCUMENTS

| | | |
|---|---|---|
| 3,713,860 A | 1/1973 | Auskern |
| 3,740,851 A | 6/1973 | Weissman |
| 3,797,113 A | 3/1974 | Brainin |
| 3,808,606 A | 5/1974 | Tronzo |
| 3,849,887 A | 11/1974 | Brainin |
| 3,851,393 A * | 12/1974 | Weiss et al. ............... 433/176 |
| 3,896,547 A | 7/1975 | Kulwiec |
| 3,905,109 A | 9/1975 | Cohen et al. |
| 3,906,550 A | 9/1975 | Rostoker et al. |
| 3,919,773 A | 11/1975 | Freeman |
| 3,934,347 A | 1/1976 | Lash et al. |
| 3,992,725 A | 11/1976 | Homsy |
| 4,011,602 A | 3/1977 | Rybicki et al. |
| 4,016,651 A | 4/1977 | Kawahara et al. |
| 4,086,701 A | 5/1978 | Kawahara et al. |
| 4,097,935 A | 7/1978 | Jarcho |
| 4,122,605 A | 10/1978 | Hirabayashi et al. |
| 4,131,597 A | 12/1978 | Bluethgen |
| 4,156,943 A | 6/1979 | Collier |
| 4,178,686 A | 12/1979 | Riess et al. |
| 4,195,366 A | 4/1980 | Jarcho et al. |
| 4,199,864 A | 4/1980 | Ashman |
| 4,229,170 A | 10/1980 | Perez |
| 4,244,689 A | 1/1981 | Ashman |
| 4,252,525 A | 2/1981 | Child |
| 4,259,072 A | 3/1981 | Hirabayashi et al. |
| 4,281,991 A | 8/1981 | Michi et al. |
| 4,283,176 A * | 8/1981 | Vajda ............... 433/173 |
| 4,321,042 A | 3/1982 | Scheicher |
| 4,331,420 A | 5/1982 | Jones |
| 4,375,967 A | 3/1983 | Schaefer |
| 4,379,694 A | 4/1983 | Riess |
| 4,381,918 A | 5/1983 | Ehmford |
| 4,411,624 A | 10/1983 | Ogino et al. |
| 4,431,420 A | 2/1984 | Adair |
| 4,439,152 A | 3/1984 | Small |
| 4,448,758 A | 5/1984 | Nagai et al. |
| 4,475,892 A | 10/1984 | Faunce |
| 4,478,904 A | 10/1984 | Ducheyne et al. |
| 4,483,678 A | 11/1984 | Nishio et al. |
| 4,492,577 A * | 1/1985 | Farris et al. ............ 433/201.1 |
| 4,531,915 A | 7/1985 | Tatum, Jr. |
| 4,531,916 A | 7/1985 | Scantlebury et al. |
| 4,536,158 A | 8/1985 | Bruins et al. |
| 4,547,327 A | 10/1985 | Bruins et al. |
| 4,548,959 A | 10/1985 | Nagai et al. |
| 4,556,534 A | 12/1985 | Burnett et al. |
| 4,708,652 A | 11/1987 | Fujiu et al. |
| 4,713,006 A | 12/1987 | Hakamatsuka et al. |
| 4,722,688 A | 2/1988 | Lonca |
| 4,731,085 A | 3/1988 | Koch |
| 4,737,411 A | 4/1988 | Graves, Jr. et al. |
| 4,743,260 A | 5/1988 | Burton |
| 4,744,757 A | 5/1988 | Adai et al. |
| 4,744,759 A | 5/1988 | Bowen |
| 4,820,157 A | 4/1989 | Salvo |
| 4,842,517 A | 6/1989 | Kawahara et al. |
| 4,871,384 A | 10/1989 | Kasuga |
| 4,872,839 A | 10/1989 | Brajnovie |
| 4,872,840 A | 10/1989 | Bori |
| 4,877,400 A | 10/1989 | Holsclaw |
| 4,880,610 A | 11/1989 | Constantz |
| 4,906,190 A | 3/1990 | Michna |
| 4,909,738 A | 3/1990 | Ai et al. |
| 4,957,554 A | 9/1990 | Mathers et al. |
| 4,957,819 A | 9/1990 | Kawahara et al. |
| 4,959,913 A | 10/1990 | Provence et al. |
| 4,960,733 A | 10/1990 | Kasuga et al. |
| 4,969,817 A | 11/1990 | Hiranuma et al. |
| 4,969,913 A | 11/1990 | Ojima |
| 4,976,738 A | 12/1990 | Frey et al. |
| 4,983,182 A | 1/1991 | Kijima et al. |
| 5,000,685 A | 3/1991 | Brajnovic |
| 5,002,488 A | 3/1991 | Homsy |
| 5,004,421 A | 4/1991 | Lazarof |
| 5,007,835 A | 4/1991 | Valen |
| 5,009,709 A | 4/1991 | Ibsen et al. |
| 5,049,074 A | 9/1991 | Otani |
| 5,055,497 A | 10/1991 | Okada et al. |
| 5,061,285 A | 10/1991 | Koch |
| 5,062,798 A | 11/1991 | Tsuge et al. |
| 5,064,731 A | 11/1991 | Miyazaki et al. |
| 5,076,789 A | 12/1991 | Tanaka |
| 5,087,200 A | 2/1992 | Brajnovic et al. |
| 5,120,340 A | 6/1992 | Ducheyne et al. |
| 5,123,844 A | 6/1992 | Wakai et al. |
| 5,125,839 A | 6/1992 | Ingber et al. |
| 5,125,971 A | 6/1992 | Nonami et al. |
| 5,139,424 A | 8/1992 | Yli-Urpo |
| 5,152,687 A | 10/1992 | Amino |
| 5,176,747 A | 1/1993 | Panzera et al. |
| 5,180,303 A | 1/1993 | Hornburg et al. |
| 5,186,626 A | 2/1993 | Tanaka |
| 5,192,325 A | 3/1993 | Kijima et al. |
| 5,194,000 A | 3/1993 | Dury |
| 5,194,001 A | 3/1993 | Salvo |
| 5,199,873 A | 4/1993 | Schulte et al. |
| 5,205,745 A | 4/1993 | Kamiya et al. |
| D336,683 S * | 6/1993 | Inoue et al. ............... D24/156 |
| 5,232,365 A | 8/1993 | Ikehara |
| 5,232,878 A | 8/1993 | Kasuga et al. |
| 5,236,458 A | 8/1993 | Ducheyne et al. |
| 5,238,405 A | 8/1993 | Marlin |
| 5,254,005 A | 10/1993 | Zuest |
| 5,282,861 A | 2/1994 | Kaplan |
| 5,282,863 A | 2/1994 | Burton |
| 5,288,232 A | 2/1994 | Panzera et al. |
| 5,306,673 A | 4/1994 | Hermansson et al. |
| 5,308,391 A | 5/1994 | Komma et al. |
| 5,310,343 A | 5/1994 | Hasegawa et al. |
| 5,312,254 A | 5/1994 | Rosenlicht |
| 5,314,334 A | 5/1994 | Panzera et al. |
| 5,342,201 A | 8/1994 | Oden |
| 5,344,318 A | 9/1994 | Wilson et al. |
| 5,344,457 A | 9/1994 | Pilliar et al. |
| 5,346,397 A | 9/1994 | Braiman |
| 5,415,546 A | 5/1995 | Cox, Sr. |
| 5,419,702 A | 5/1995 | Beaty et al. |
| 5,425,639 A | 6/1995 | Anders |
| 5,425,640 A | 6/1995 | Scharf |
| 5,427,527 A | 6/1995 | Niznick et al. |
| 5,439,380 A | 8/1995 | Marlin |
| 5,443,515 A | 8/1995 | Cohen et al. |
| 5,449,291 A | 9/1995 | Lueschen et al. |
| 5,458,488 A | 10/1995 | Chalifoux |
| 5,468,544 A | 11/1995 | Marcolongo et al. |
| 5,476,383 A | 12/1995 | Beaty et al. |
| 5,549,123 A | 8/1996 | Okuyama et al. |
| 5,554,665 A | 9/1996 | Tateosian et al. |
| 5,562,733 A | 10/1996 | Weissbach et al. |
| 5,571,016 A | 11/1996 | Ingber et al. |
| 5,572,652 A | 11/1996 | Robusto et al. |
| 5,575,652 A | 11/1996 | Gaffar et al. |
| 5,584,693 A | 12/1996 | Nishihara |
| 5,591,030 A | 1/1997 | Thiel et al. |
| 5,612,049 A | 3/1997 | Li et al. |
| 5,614,330 A | 3/1997 | Panzera et al. |
| 5,621,035 A | 4/1997 | Lyles et al. |
| 5,624,262 A | 4/1997 | Yarovesky et al. |
| 5,636,989 A * | 6/1997 | Somborac et al. ............ 433/173 |
| 5,645,934 A | 7/1997 | Marcolongo et al. |
| 5,674,069 A | 10/1997 | Osorio |
| 5,676,745 A | 10/1997 | Kelly et al. |
| 5,683,249 A | 11/1997 | Ibsen et al. |
| 5,685,714 A | 11/1997 | Beaty et al. |
| 5,695,337 A | 12/1997 | Tyszblat Sadoun |
| 5,697,785 A | 12/1997 | Delahaye |
| 5,697,976 A | 12/1997 | Chesterfield et al. |
| 5,697,997 A | 12/1997 | Aronsson et al. |
| 5,698,019 A | 12/1997 | Frank et al. |
| 5,702,346 A | 12/1997 | Lazzara et al. |
| 5,713,994 A | 2/1998 | Kramer et al. |
| 5,723,007 A | 3/1998 | Engel et al. |
| 5,727,943 A | 3/1998 | Beaty et al. |

(56) References Cited

U.S. PATENT DOCUMENTS

| | | |
|---|---|---|
| 5,755,809 A | 5/1998 | Cohen et al. |
| 5,759,036 A | 6/1998 | Hinds |
| 5,762,500 A | 6/1998 | Lazarof |
| 5,772,438 A | 6/1998 | Deom |
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,947,893 A | 9/1999 | Agrawal et al. |
| 5,951,290 A | 9/1999 | Ardizio et al. |
| 5,951,293 A | 9/1999 | Billet et al. |
| 5,951,295 A | 9/1999 | Lyles et al. |
| 5,961,328 A | 10/1999 | Somborac et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,214,368 B1 | 4/2001 | Lee et al. |
| 6,224,662 B1 | 5/2001 | Nemeth |
| 6,227,857 B1 | 5/2001 | Morgan et al. |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,302 B1 | 1/2002 | Steidl et al. |
| 6,342,458 B1 | 1/2002 | Schweiger et al. |
| 6,343,930 B1 | 2/2002 | Beaty et al. |
| 6,345,836 B1 | 2/2002 | Wu |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinghoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,998 B2 | 12/2005 | Rizzo et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 7,011,522 B2 | 3/2006 | Panzera et al. |
| 7,291,012 B2 | 11/2007 | Lyren |
| 7,718,100 B2 | 5/2010 | Soler et al. |
| 8,075,312 B2 | 12/2011 | Collins et al. |
| 8,562,346 B2 | 10/2013 | Collins et al. |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0095123 A1 | 7/2002 | Smutney et al. |
| 2002/0095213 A1 | 7/2002 | Bakker et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli et al. |
| 2004/0024081 A1 | 2/2004 | Trieu et al. |
| 2004/0058299 A1 | 3/2004 | Molin et al. |

(56) References Cited

U.S. PATENT DOCUMENTS

| | | | |
|---|---|---|---|
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0185420 A1 | 9/2004 | Schulter |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0008990 A1 | 1/2005 | Ganz et al. |
| 2005/0014108 A1 | 1/2005 | Wohrle et al. |
| 2005/0023710 A1 | 2/2005 | Brodkin et al. |
| 2005/0031704 A1 | 2/2005 | Ahn |
| 2005/0084533 A1 | 4/2005 | Howdle et al. |
| 2005/0084819 A1 | 4/2005 | Sims |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |
| 2005/0123672 A1 | 6/2005 | Justin et al. |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0075826 A1 | 4/2006 | Roberts et al. |
| 2006/0105295 A1 | 5/2006 | Mayer et al. |
| 2007/0015110 A1 | 1/2007 | Zhang |
| 2007/0111165 A1 | 5/2007 | Wallick |
| 2007/0118221 A1 | 5/2007 | Robie et al. |
| 2007/0148621 A1 | 6/2007 | Yakir |
| 2007/0184265 A1 | 8/2007 | Ranganathan et al. |
| 2008/0050699 A1 | 2/2008 | Zhang |
| 2008/0241793 A1 | 10/2008 | Collins |
| 2008/0280254 A1 | 11/2008 | Ackermann |
| 2009/0011384 A1 | 1/2009 | Collins et al. |
| 2009/0036908 A1 | 2/2009 | Zokol et al. |
| 2009/0093888 A1 | 4/2009 | Dawson et al. |
| 2009/0098510 A1 | 4/2009 | Zhang |
| 2009/0098511 A1 | 4/2009 | Zhang |
| 2013/0323677 A1* | 12/2013 | Pearson .................. 433/173 |
| 2013/0344457 A1 | 12/2013 | Collins et al. |

FOREIGN PATENT DOCUMENTS

| | | |
|---|---|---|
| CA | 2620427 C | 3/2014 |
| DE | 3110694 A1 | 9/1982 |
| DE | 4209569 C2 | 11/1994 |
| DE | 19508224 A1 | 9/1995 |
| DE | 19529036 | 3/1997 |
| DE | 10105398 | 8/2002 |
| DE | 10105398 A1 | 8/2002 |
| EP | 0266313 | 5/1988 |
| EP | 0271236 | 6/1988 |
| EP | 0333503 | 9/1989 |
| EP | 0950421 | 10/1989 |
| EP | 0345581 | 12/1989 |
| EP | 0366018 | 5/1990 |
| EP | 0366018 A1 | 5/1990 |
| EP | 0417018 | 3/1991 |
| EP | 0467948 | 1/1992 |
| EP | 0498923 | 8/1992 |
| EP | 0333503 A2 | 2/1993 |
| EP | 056027 | 9/1993 |
| EP | 0560279 A1 | 9/1993 |
| EP | 560279 A1 | 9/1993 |
| EP | 0806211 | 5/1996 |
| EP | 1281372 | 5/1996 |
| EP | 1598028 | 11/2005 |
| EP | 1712205 A2 | 10/2006 |
| FR | 2796265 | 1/2001 |
| FR | 2796265 A1 | 1/2001 |
| GB | 701802 A | 1/1954 |
| GB | 1526780 | 9/1978 |
| GB | 1526780 A1 | 9/1978 |
| GB | 2199626 A | 7/1988 |
| GB | 2401867 | 11/2004 |
| GB | 2416996 | 2/2006 |
| GB | 2416996 A1 | 2/2006 |
| JP | 61275205 | 12/1986 |
| JP | 63290559 | 11/1988 |
| JP | 1025849 | 1/1989 |
| JP | 1159832 U | 11/1989 |
| JP | 3292948 A | 12/1991 |
| JP | 7255832 A | 10/1995 |
| JP | 9313505 A | 12/1997 |
| JP | 2000501966 A | 2/2000 |
| JP | 2000514329 A | 10/2000 |
| JP | 2001518348 A | 10/2001 |
| JP | 2002126071 | 5/2002 |
| WO | WO-8604807 A1 | 8/1986 |
| WO | 8900410 | 1/1989 |
| WO | WO-8900410 A1 | 1/1989 |
| WO | 90/11979 | 10/1990 |
| WO | WO-9011979 A1 | 10/1990 |
| WO | 93/20773 | 10/1993 |
| WO | 94/21190 | 9/1994 |
| WO | WO-9421190 A1 | 9/1994 |
| WO | 9528973 | 11/1995 |
| WO | WO-9528973 A1 | 11/1995 |
| WO | 97/21393 | 6/1997 |
| WO | WO-9721393 A1 | 6/1997 |
| WO | WO-9722308 A1 | 6/1997 |
| WO | 97/41809 | 11/1997 |
| WO | WO-9741809 A1 | 11/1997 |
| WO | WO-9801081 A1 | 1/1998 |
| WO | 9830170 | 7/1998 |
| WO | WO-9830170 A1 | 7/1998 |
| WO | WO-9917676 A2 | 5/1999 |
| WO | 0021455 | 4/2000 |
| WO | WO-0021455 A1 | 4/2000 |
| WO | 01/32072 | 5/2001 |
| WO | WO-0132072 A2 | 5/2001 |
| WO | 01/87193 | 11/2001 |
| WO | WO-0187193 A1 | 11/2001 |
| WO | 0234155 | 2/2002 |
| WO | 02/36039 | 5/2002 |
| WO | WO-0234155 A1 | 5/2002 |
| WO | WO-0236039 A1 | 5/2002 |
| WO | 02/062901 | 8/2002 |
| WO | 02/064100 | 8/2002 |
| WO | 03/065996 | 5/2003 |
| WO | 03/065939 | 8/2003 |
| WO | WO-03065939 A1 | 8/2003 |
| WO | WO-03065996 A2 | 8/2003 |
| WO | 03/078508 | 9/2003 |
| WO | 03/094774 | 11/2003 |
| WO | 2004/054464 | 7/2004 |
| WO | WO-2004054464 A2 | 7/2004 |
| WO | 2004/103202 | 12/2004 |
| WO | WO-2004103202 A1 | 12/2004 |
| WO | 2007027794 | 3/2006 |
| WO | 2006/082610 | 8/2006 |
| WO | WO-2006082610 A2 | 8/2006 |
| WO | 2007027794 A1 | 3/2007 |
| WO | WO-2007027794 A1 | 3/2007 |
| WO | 2007/086832 | 8/2007 |
| WO | WO-2007086832 A2 | 8/2007 |
| WO | WO-2009029711 A1 | 3/2009 |
| WO | WO-2009029718 A1 | 3/2009 |
| WO | WO-2009032759 A1 | 3/2009 |
| WO | WO-2009032766 A1 | 3/2009 |
| WO | WO-2010002661 A2 | 1/2010 |
| WO | WO-2010002661 A3 | 1/2010 |

OTHER PUBLICATIONS

Shape Optimization of Randomly Oriented Short Fibers for Bone Cement Reinforcements, Yan Zhou, Chaodi Li, James J. Mason, Materials Science & Engineering A 393 (2005) 374-381.
Flocculants, Binders, and Bonds, Chapter 11, Molecular Binders pp. 173-177.

(56) References Cited

OTHER PUBLICATIONS

Injection Molding, Chapter 24, Equipment and Material Variables in Injection Molding, pp. 479-481.
An Introduction to Silanes and Their Clinical Applications in Dentistry, Jukka P.I Matinlinna et al., vol. 17, No. 2, 2004 pp. 155-164 The International Journal of Prosthodontics.
Innovative Ceramic-Fiber Technology Energizes Advanced Cerametrics, Richard B. Cass et al. Story—The American Ceramic Society, American Ceramic Society Bulletin, Nov. 2003, pp. 9701-9706.
PEEK-CLASSIX, Information Sheet Invibio Ltd., Properties of PEEK-CLASSIX White Granular.
The Clinical Assessment of a Ceramic-Coated Transmucosal Dental Implant Collar; International Journal of Prosthodonics; 1996—vol. , Issue 5; pp. 466-472.
Two Applications of Transmucosal Milled Ceramic in Implantology; Preliminary Clinical Examples; Implant Quintessence Dentistry International; Aug. 1996—vol. 27, Issue 8, pp. 533-547.
International Search Report from related PCT/US2008/074655; Feb. 18, 2009; 9 pages.
"U.S. Appl. No. 11/847,476, Examiner Interview Summary mailed Nov. 14, 2012", 3 pgs.
"U.S. Appl. No. 11/847,476, Response filed Nov. 27, 2012 to Final Office Action mailed Jul. 13, 2012", 22 pgs.
"U.S. Appl. No. 12/167,018, Final Office Action mailed Jun. 14, 2012", 19 pgs.
"U.S. Appl. No. 12/167,018, Response filed Nov. 9, 2012 to Final Office Action mailed Jun. 14, 2012", 17 pgs.
"U.S. Appl. No. 12/167,049, Final Office Action mailed Dec. 17, 2012", 11 pgs.
"U.S. Appl. No. 12/167,049, Notice of Allowance mailed Jun. 24, 2013", 6 pgs.
"U.S. Appl. No. 12/167,049, Response filed Apr. 17, 2013 to Non Final Office Action mailed Dec. 17, 2012", 15 pgs.
"U.S. Appl. No. 12/167,049, Response filed Aug. 28, 2012 to Non Final Office Action mailed Mar. 28, 2012", 18 pgs.
"U.S. Appl. No. 14/010,634, Preliminary Amendment filed Aug. 27, 2013", 3 pgs.
"Australian Application Serial No. 2006284874, Office Action mailed Jul. 26, 2011", 4 pgs.
"Australian Application Serial No. 2006284874, Preliminary Amendment mailed May 6, 2008", 12 pgs.
"Australian Application Serial No. 2006284874, Preliminary Amendment mailed Oct. 20, 2010", 15 pgs.
"Australian Application Serial No. 2006284874, Response filed Oct. 27, 2011 to Office Action mailed Jul. 26, 2011", 10 pgs.
"Canadian Application Serial No. 2,620,427, Office Action mailed Jan. 7, 2013", 3 pgs.
"Canadian Application Serial No. 2,620,427, Response filed Jul. 4, 2013 to Office Action mailed Jan. 7, 2013", 8 pgs.
"European Application Serial No. 06813974.0, Preliminary Amendment filed Mar. 19, 2008", 2 pgs.
"European Application Serial No. 08798879.6, Office Action mailed May 7, 2010", 2 pgs.
"European Application Serial No. 08798879.6, Preliminary Amendment filed Mar. 30, 2010", 4 pgs.
"European Application Serial No. 08828199.3, Preliminary Amendment filed Mar. 29, 2010", 2 pgs.
"European Application Serial No. 08828675.2, Preliminary Amendment filed Mar. 29, 2010", 2 pgs.
"European Application Serial No. 08829319.6, Preliminary Amendment filed Mar. 29, 2010", 3 pgs.
"European Application Serial No. 09774112.8, Office Action mailed Mar. 27, 2013", 6 pgs.
"European Application Serial No. 09774112.8, Response filed Aug. 6, 2013 to Office Action mailed Mar. 27, 2013", 16 pgs.
"Japanese Application Serial No. 2008-529238, Response filed Mar. 29, 2013 to Office Action mailed Oct. 23, 2012", (W/ English Translation), 7 pgs.
"Japanese Application Serial No. 2008-529238, Office Action mailed Aug. 20, 2013", (W/ English Translation), 7 pgs.
"Japanese Application Serial No. 2008-529238, Office Action mailed Oct. 23, 2012", (W/ English Translation), 11 pgs.
"U.S. Appl. No. 11/847,476, Final Office Action mailed Jul. 13, 2012", 7 pgs.
"U.S. Appl. No. 11/847,476, Final Office Action mailed Dec. 8, 2010", 7 pgs.
"U.S. Appl. No. 11/847,476, Non Final Office Action mailed Jan. 26, 2012", 6 pgs.
"U.S. Appl. No. 11/847,476, Non Final Office Action mailed Jun. 24, 2010", 7 pgs.
"U.S. Appl. No. 11/847,476, Non Final Office Action mailed Jul. 11, 2011", 7 pgs.
"U.S. Appl. No. 11/847,476, Response filed Apr. 8, 2011 to Final Office Action mailed Dec. 8, 2010", 15 pgs.
"U.S. Appl. No. 11/847,476, Response filed Apr. 26, 2012 to Non Final Office Action mailed Jan. 26, 2012", 12 pgs.
"U.S. Appl. No. 11/847,476, Response filed Apr. 29, 2010 to Restriction Requirement mailed Mar. 29, 2010", 2 pgs.
"U.S. Appl. No. 11/847,476, Response filed Sep. 17, 2010 to Non Final Office Action mailed Jun. 24, 2010", 12 pgs.
"U.S. Appl. No. 11/847,476, Response filed Nov. 10, 2011 to Non Final Office Action mailed Jul. 11, 2011", 12 pgs.
"U.S. Appl. No. 11/847,476, Restriction Requirement mailed Mar. 29, 2010", 9 pgs.
"U.S. Appl. No. 12/065,259, Final Office Action mailed Dec. 9, 2010", 8 pgs.
"U.S. Appl. No. 12/065,259, Non Final Office Action mailed Apr. 27, 2011", 8 pgs.
"U.S. Appl. No. 12/065,259, Non Final Office Action mailed Dec. 21, 2009", 8 pgs.
"U.S. Appl. No. 12/065,259, Notice of Allowance mailed Sep. 16, 2011", 7 pgs.
"U.S. Appl. No. 12/065,259, Response filed Apr. 7, 2011 to Final Office Action mailed Dec. 9, 2010", 10 pgs.
"U.S. Appl. No. 12/065,259, Response filed Jun. 18, 2010 to Non Final Office Action mailed Dec, 21, 2009", 9 pgs.
"U.S. Appl. No. 12/065,259, Response filed Jun. 30, 2011 to Non Final Office Action mailed Apr. 27, 2011", 8 pgs.
"U.S. Appl. No. 12/065,259, Response filed Sep. 30, 2010 to Restriction Requirement mailed Aug. 31, 2010", 7 pgs.
"U.S. Appl. No. 12/065,259, Restriction Requirement mailed Aug. 31, 2010", 5 pgs.
"U.S. Appl. No. 12/167,004, Examiner Interview Summary mailed Mar. 2, 2012", 3 pgs.
"U.S. Appl. No. 12/167,004, Final Office Action mailed Nov. 9, 2011", 16 pgs.
"U.S. Appl. No. 12/167,004, Non Final Office Action mailed Feb. 13, 2012", 17 pgs.
"U.S. Appl. No. 12/167,004, Non Final Office Action mailed May 24, 2011", 17 pgs.
"U.S. Appl. No. 12/167,004, Non Final Office Action mailed Nov. 10, 2010", 12 pgs.
"U.S. Appl. No. 12/167,004, Response filed Feb. 9, 2012 to Final Office Action mailed Nov. 9, 2011", 15 pgs.
"U.S. Appl. No. 12/167,004, Response filed Mar. 10, 2011 to Non Final Office Action mailed Nov. 10, 2010", 14 pgs.
"U.S. Appl. No. 12/167,004, Response filed Aug. 24, 2011 to Non Final Office Action mailed May 24, 2011", 13 pgs.
"U.S. Appl. No. 12/167,004, Response filed Oct. 11, 2010 to Restriction Requirement mailed Sep. 14, 2010", 6 pgs.
"U.S. Appl. No. 12/167,004, Restriction Requirement mailed Sep. 14, 2010", 4 pgs.
"U.S. Appl. No. 12/167,018, Examiner Interview Summary mailed Oct. 23, 2012", 3 pgs.
"U.S. Appl. No. 12/167,018, Final Office Action mailed May 23, 2011", 22 pgs.
"U.S. Appl. No. 12/167,018, Non Final Office Action mailed Aug. 30, 2011", 20 pgs.
"U.S. Appl. No. 12/167,018, Non Final Office Action mailed Nov. 18, 2010", 22 pgs.

(56) References Cited

OTHER PUBLICATIONS

"U.S. Appl. No. 12/167,018, Response filed Mar. 18, 2011 to Non Final Office Action mailed Nov. 18, 2010", 11 pgs.
"U.S. Appl. No. 12/167,018, Response filed Aug. 23, 2011 to Final Office Action mailed May 23, 2011", 11 pgs.
"U.S. Appl. No. 12/167,018, Response filed Oct. 27, 2010 to Restriction Requirement mailed Aug. 30, 2010", 6 pgs.
"U.S. Appl. No. 12/167,018, Response filed Nov. 22, 2011 to Non Final Office Action mailed Aug. 30, 2011", 10 pgs.
"U.S. Appl. No. 12/167,018, Restriction Requirement mailed Aug. 30, 2010", 6 pgs.
"U.S. Appl. No. 12/167,049, Applicant's Summary of Examiner Interview filed Feb. 9, 2012", 2 pgs.
"U.S. Appl. No. 12/167,049, Examiner Interview Summary mailed Jan. 26, 2011", 3 pgs.
"U.S. Appl. No. 12/167,049, Examiner Interview Summary mailed Jun. 29, 2012", 3 pgs.
"U.S. Appl. No. 12/167,049, Final Office Action mailed Aug. 31, 2010", 12 pgs.
"U.S. Appl. No. 12/167,049, Non Final Office Action mailed Mar. 28, 2012", 12 pgs.
"U.S. Appl. No. 12/167,049, Non Final Office Action mailed Dec. 18, 2009", 8 pgs.
"U.S. Appl. No. 12/167,049, Preliminary Amendment filed Jul. 3, 2008", 3 pgs.
"U.S. Appl. No. 12/167,049, Response filed Feb. 8, 2011 to Final Office Action mailed Aug. 31, 2010", 19 pgs.
"U.S. Appl. No. 12/167,049, Response filed Jun. 15, 2010 to Non Final Office Action mailed Dec. 18, 2009", 8 pgs.
"European Application Serial No. 06813974.0, European Search Report mailed Jan. 12, 2010", 5 pgs.
"European Application Serial No. 06813974.0, Office Action mailed Apr. 8, 2008", 2 pgs.
"European Application Serial No. 06813974.0, Office Action mailed Apr. 14, 2010", 1 pg.
"European Application Serial No. 06813974.0, Response filed Oct. 21, 2010 to Office Action mailed Apr. 14, 2010", 17 pgs.
"European Application Serial No. 08828199.3, Office Action mailed May 11, 2010", 2 pgs.
"European Application Serial No. 08828199.3, Response filed Jun. 18, 2010 to Office Action mailed May 11, 2010", 9 pgs.
"European Application Serial No. 08828675.2, Office Action mailed May 11, 2010", 2 pgs.
"European Application Serial No. 08828675.2, Response filed Jun. 17, 2010 to Office Action mailed May 11, 2010", 2 pgs.
"European Application Serial No. 09774112.8, Office Action mailed Feb. 17, 2011", 2 pgs.
"European Application Serial No. 09774112.8, Office Action mailed Mar. 16, 2011", 1 pg.
"European Application Serial No. 09774112.8, Response filed Mar. 28, 2011 to Office Action mailed Feb. 17, 2011", 6 pgs.
"International Application Serial No. PCT/US2006/020130, International Search Report mailed Feb. 6, 2007", 10 pgs.
"International Application Serial No. PCT/US2006/033893, International Preliminary Report on Patentability mailed Mar. 4, 2008", 4 pgs.
"International Application Serial No. PCT/US2006/033893, International Search Report mailed Jan. 29, 2007", 1 pg.
"International Application Serial No. PCT/US2006/033893, Written Opinion mailed Jan. 29, 2007", 3 pgs.
"International Application Serial No. PCT/US2007/069562, International Search Report mailed Jul. 7, 2008", 1 pg.
"International Application Serial No. PCT/US2008/074616, International Preliminary Report on Patentability mailed Mar. 2, 2010", 6 pgs.
"International Application Serial No. PCT/US2008/074616, International Search Report mailed Dec. 16, 2008", 4 pgs.
"International Application Serial No. PCT/US2008/074616, Written Opinion mailed Dec. 16, 2008", 5 pgs.
"International Application Serial No. PCT/US2008/074642, International Preliminary Report on Patentability mailed Mar. 2, 2010", 5 pgs.
"International Application Serial No. PCT/US2008/074642, International Search Report mailed Feb. 12, 2009", 4 pgs.
"International Application Serial No. PCT/US2008/074642, Written Opinion mailed Feb. 12, 2009", 4 pgs.
"International Application Serial No. PCT/US2008/074645, International Preliminary Report on Patentability mailed Mar. 2, 2010", 6 pgs.
"International Application Serial No. PCT/US2008/074645, International Search Report mailed Dec. 29, 2008", 5 pgs.
"International Application Serial No. PCT/US2008/074645, Written Opinion mailed Dec. 29, 2008", 5 pgs.
"International Application Serial No. PCT/US2008/074655, International Preliminary Report on Patentability mailed Mar. 2, 2010", 6 pgs.
"International Application Serial No. PCT/US2008/074655, International Search Report mailed Feb. 18, 2009", 9 pgs.
"International Application Serial No. PCT/US2008/074655, Written Opinion mailed Feb. 18, 2009", 5 pgs.
"International Application Serial No. PCT/US2009/048456, International Preliminary Report on Patentability mailed Jan. 5, 2011", 7 pgs.
"International Application Serial No. PCT/US2009/048456, International Search Report mailed Apr. 27, 2010", 5 pgs.
"International Application Serial No. PCT/US2009/048456, Written Opinion mailed Apr. 27, 2010", 6 pgs.
"International Application Serial No. PCT/US2009/048469, International Search Report mailed Oct. 19, 2009", 3 pgs.
"International Application Serial No. PCT/US2009/048469, International Search Report mailed Oct. 19, 2009", 9 pgs.
"International Application Serial No. PCT/US2009/048469, Written Opinion mailed Oct. 19, 2009", 6 pgs.
"International Application Serial No. PCT/US2009/048476, International Search Report mailed Dec. 10, 2009", 4 pgs.
"International Application Serial No. PCT/US2009/048476, International Search Report mailed Dec. 10, 2009", 13 pgs.
"International Application Serial No. PCT/US2009/048476, Written Opinion mailed Dec. 10, 2009", 6 pgs.
"International Application Serial No. PCT/US2009/048481, International Search Report mailed Dec. 10, 2009", 3 pgs.
"International Application Serial No. PCT/US2009/048481, Written Opinion mailed Dec. 10, 2009", 7 pgs.
"International Application Serial No. PCT/US2009/062308, International Search Report mailed Jan. 21, 2010", 6 pgs.
"International Application Serial No. PCT/US2009/062308, Written Opinion mailed Jan. 21, 2010", (Oct. 28, 2009), 8 pgs.
"Japanese Application Serial No. 2008-529238, Office Action mailed Jan. 10, 2012", (W/ English Translation), 4 pgs.
"Japanese Application Serial No. 2008-529238, Response filed Apr. 2012 to Office Action mailed Jan. 10, 2012", (W/ English Translation), 9 pgs.
Cass, Richard B, et al., "Innovative Ceramic-Fiber Technology Energizes Advanced Cerametrics", The American Ceramic Society, American Ceramics Society Bulletin, (Nov. 2003), 9701-9706.
Ganz, Scott D, "Presurgical Planning With CT-Derived Fabrication of Surgical Guides", J Oral Maxiofac Surg 63, Suppl 2, (2005), 59-73 pgs.
Kan, Joseph Y K, "Computer-Guided Immediate Provisionalization of Anterior Multiple Adjacent Implants: Surgical and Prosthodontic Rationale", Practical Procedures & Aethetic Dentistry, vol. 18, No. 10, (2006), 617-623 pgs.
Rosenfeld, Alan L, "Prosthetically Directed Implant Placement Using Computer Software to Ensure Precise Placement and Predictable Prosthetic Outcomes. Part 1: Diagnostics, Imaging, and Collaborative Accountability", International Journal of Periodontics & Restorative Dentistry, vol. 26, No. 3, (2006), 215-221 pgs.
"U.S. Appl. No. 11/847,476, Examiner Interview Summary mailed Feb. 3, 2014", 3 pgs.
"U.S. Appl. No. 11/847,476, Non Final Office Action mailed Nov. 5, 2013", 8 pgs.

(56) References Cited

OTHER PUBLICATIONS

"U.S. Appl. No. 12/167,018, Final Office Action mailed Feb. 20, 2014", 9 pgs.
"U.S. Appl. No. 12/167,018, Non Final Office Action mailed Nov. 6, 2013", 9 pgs.
"U.S. Appl. No. 12/167,018, Response filed Feb. 4, 2014 to Non-Final Office Action dated Nov. 6, 2013", 14 pgs.
"U.S. Appl. No. 14/010,634, Non Final Office Action mailed Dec. 19, 2013", 10 pgs.
"European Application Serial No. 06813974.0, Examination Notification Art. 94(3) mailed Sep. 19, 2013", 4 pgs.
"European Application Serial No. 08827534.2, Response filed Jan. 28, 2014 to Office Action mailed Sep. 19, 2013", 9 pgs.
"Japanese Application Serial No. 2008-529238, Response filed Nov. 18, 2013 to Office Action mailed Aug. 20, 2013", (W/ English Translation of Claims), 6 pgs.
"U.S. Appl. No. 11/847,476, Notice of Allowance mailed Apr. 17, 2014", 7 pgs.
"U.S. Appl. No. 11/847,476, Response filed Mar. 5, 2014 to Non-Final Office Action mailed Nov. 5, 2013", 32 pgs.
"U.S. Appl. No. 12/167,018, Advisory Action mailed Apr. 24, 2014", 2 pgs.
"U.S. Appl. No. 12/167,018, Response filed Apr. 9, 2014 to Final Office Action mailed Feb. 20, 2014", 15 pgs.
"U.S. Appl. No. 14/010,634, Response filed May 20, 2014 to Non-Final Office Action mailed Dec. 19, 2013", 11 pgs.
Computer-Guided Immediate Provisionalization of Anterior Multiple Adjacent Implants: Surgical and Prosthodontic Rationale, Joseph Y. K. Kan, Practical Procedures & Aethetic Dentistry, vol. 18, No. 10, 617-623, 2006.
Presurgical Planning With CT-Derived Fabrication of Surgical Guides, Scott D. Ganz, J Oral Maxillofac Surg 63:59-73, 2005, Suppl 2.
Prosthetically Directed Implant Placement ing Computer Software to Ensure Precise Placement and Predictable Prosthetic Outcomes. Part 1: Diagnostics, Imaging, and Collaborative Accountability, Alan L. Rosenfeld, International Journal of Periodontics & Restorative Dentistry, vol. 26, No. 3, 2006, 215-221.
International Search Report from related application PCT/2006/033893, dated Jan. 29, 2007, 1 page.
International Search Report from related application PCT/2006/020130, dated Feb. 6, 2007, 10 pages.
International Search Report from related application PCT/2007/069562, dated Jul. 7, 2008, 1 page.
International Search Report from related application PCT/2008/074616; dated Dec. 16, 2008; 4 pages.
International Search Report from related application PCT/2008/074642; dated Feb. 12, 2009, 4 pages.
International Search Report from related application PCT/2009/048469, dated Oct. 19, 2009, 9 pages.
International Search Report from related application PCT/2009/048476; dated Dec. 10, 2009; 13 pages.
International Search Report from related application PCT/2009/048481; dated Dec. 10, 2009; 13 pages.
International Search Report from related application PCT/2009/062308; dated Jan. 21, 2010; 17 pages.
International Search Report from related application PCT/2009/048456; dated Apr. 27, 2010; 5 pages.

* cited by examiner

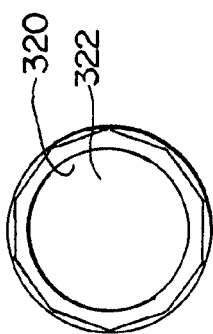
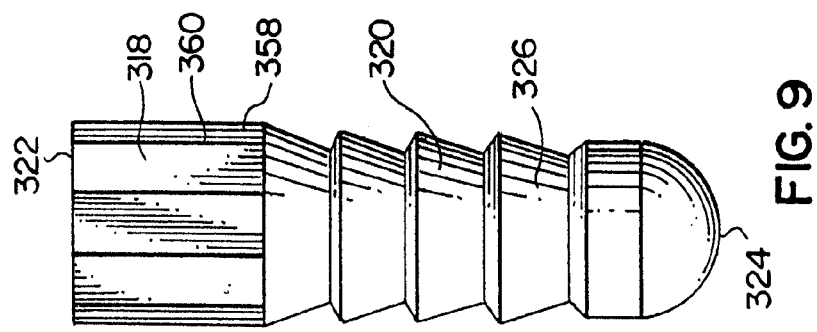
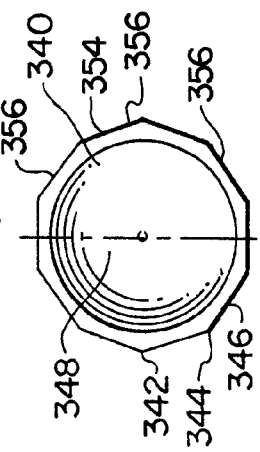
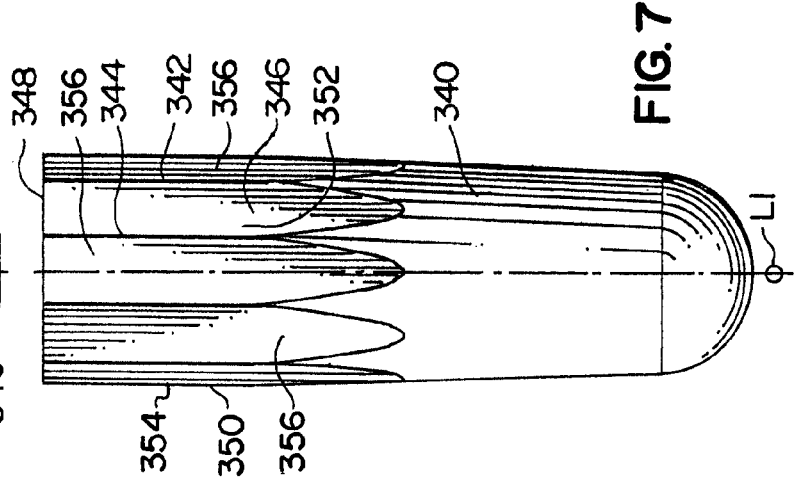
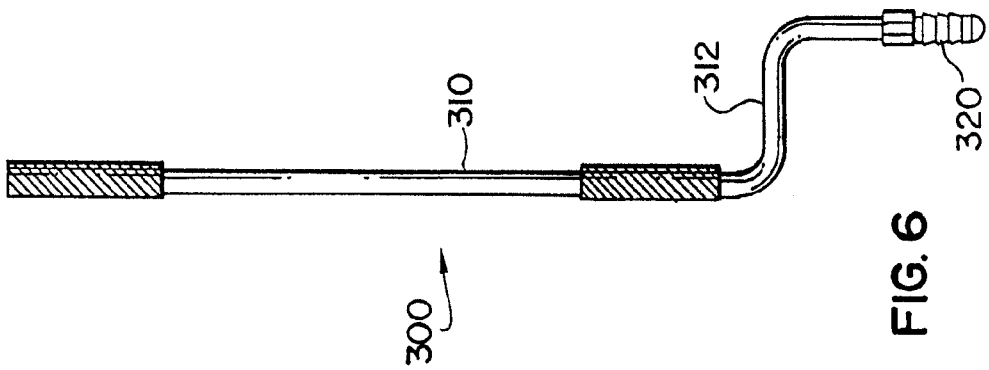

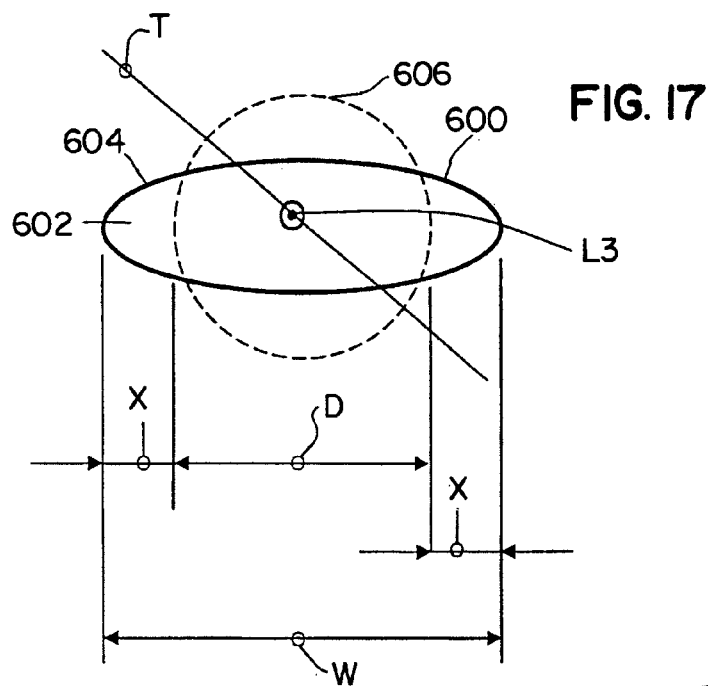
FIG. 17
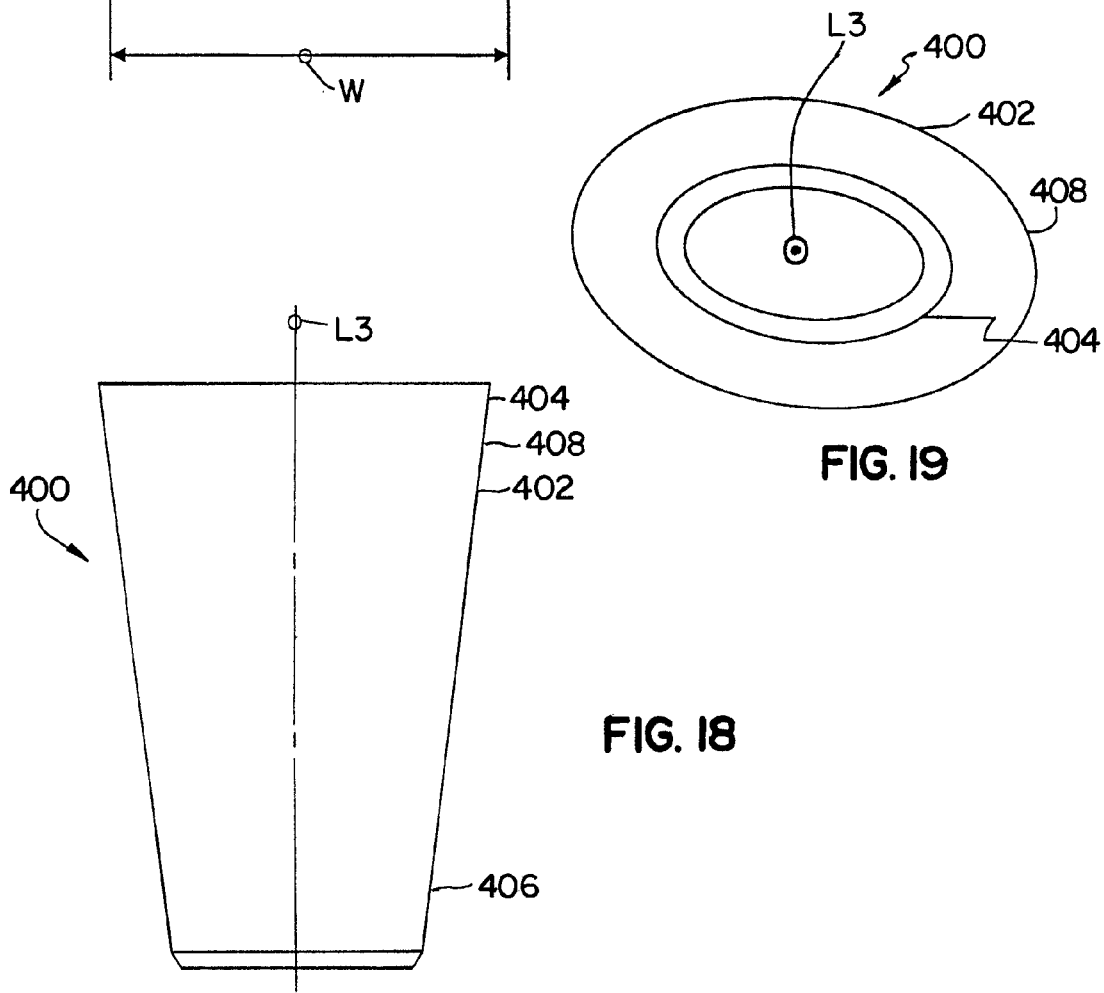
FIG. 19
FIG. 18

MULTIPLE ROOT IMPLANT

CROSS-REFERENCE TO RELATED APPLICATIONS

This application is a continuation-in-part of pending U.S. patent application Ser. No. 11/847,476, filed Aug. 30, 2007, which is incorporated herein by reference in its entirety for all purposes.

FIELD OF INVENTION

The present invention relates to bone implant prosthetic devices and, in particular, to a dental prosthetic device with a shape for resisting torsional force applied to the device.

BACKGROUND

A dental implant or fixture is surgically implanted into a patient's upper or lower jaw to directly or indirectly anchor and support prosthetic devices, such as an artificial tooth. The implants are usually placed at one or more edentulous sites in a patient's dentition at which the patient's original teeth have been lost or damaged in order to restore the patient's chewing function. In many cases, the implant anchors a dental abutment, which in turn provides an interface between the implant and a dental restoration. The restoration is typically a porcelain crown fashioned according to known methods.

One form of a prosthetic device is a unitary or one-piece implant device with a bone-engaging implant portion and an abutment portion integral with the implant portion. Another form of a prosthetic device is a multiple piece device where the abutment is assembled onto the implant. A desire still exists, however, to improve the osseointegration characteristics of such dental devices.

One problem with one-piece dental devices is that the titanium and other materials used for such devices often are an unattractive color. Thus, when the abutment portion of the device below a prosthetic tooth but above the gum or gingival tissue is visible and does not have the color of natural teeth, the dental device provides a non-esthetically pleasing appearance in a person's mouth. Other known dental devices that have the color of natural teeth typically provide inadequate strength resulting in relatively frequent replacement or repair of the device.

Whether or not the dental implant device is a one-piece or part of a multiple piece device where the abutment is assembled onto the implant, the implant is usually either threaded or press-fit into a bore which is drilled into the patient's mandible or maxilla at the edentulous site. The press-fit implant is inserted by applying a force to the coronal end of the implant in an insertion direction. For a threaded implant, self-tapping threads may be provided for initial stability of the implant immediately after surgery. Before biologic integration has time to take place, the threads resist tension, twisting, or bending loads applied to the implant. Additionally, patients prefer to leave the initial surgery with some type of restoration and it has further been shown that the healing of the soft and hard bone tissue is improved if the implant is loaded after surgery.

The surgical procedure for inserting the threaded implants, however, can be complicated and requires that the threaded implants be turned into place, which further requires the use of special tools and inserts. The torque needed to place the implant into the jaw can be high and may require tapping of the bore on the jaw, which adds yet another step to the surgical procedure where tapping typically is not desired. Also with threaded implants, it is often difficult to achieve optimal esthetics where, for example, a prosthetic is held at an ideal orientation by the implant because the geometry of the thread establishes a fixed relationship between the final vertical and rotational orientation of the implant such that a vertical adjustment requires a rotational adjustment and vice-versa.

Alternatively, a press fit implant has a much simpler surgical procedure. For a press fit implant, the implant is inserted by applying a force to the coronal end of the implant in an insertion direction. Unlike the self-tapping, threaded dental implants, however, the current press fit designs provide insufficient frictional contact with the bore to adequately restrict the rotation of the implant within the bore or prevent the implant from pulling out of the bore that can be caused by mastication forces. Thus, the current press fit designs provide very little initial stability and are not well suited for early and immediate loading procedures that are currently used in dentistry. A desire still exists, therefore, to provide press fit implants with greater resistance to mastication forces.

BRIEF DESCRIPTION OF THE DRAWINGS

FIG. 6 is a side elevational view of an instrument used to aid in press-fitting an implant into a jaw bone in accordance with the present invention;

FIG. 7 is a side elevational view of an alternative implant configured for press-fitting in accordance with the present invention;

FIG. 8 is a top view of the alternative implant of FIG. 7;

FIG. 9 is a side elevational view of another implant configured for press-fitting in accordance with the present invention;

FIG. 10 is a top view of the implant of FIG. 9;

FIG. 17 is a simplified and exaggerated top cross-sectional view taken along line XVII-XVII on FIG. 16;

FIG. 18 is a side elevational view of another implant configured for press-fitting in accordance with the present invention;

FIG. 19 is a top view of the implant in FIG. 18;

DETAILED DESCRIPTION

Figure 1:
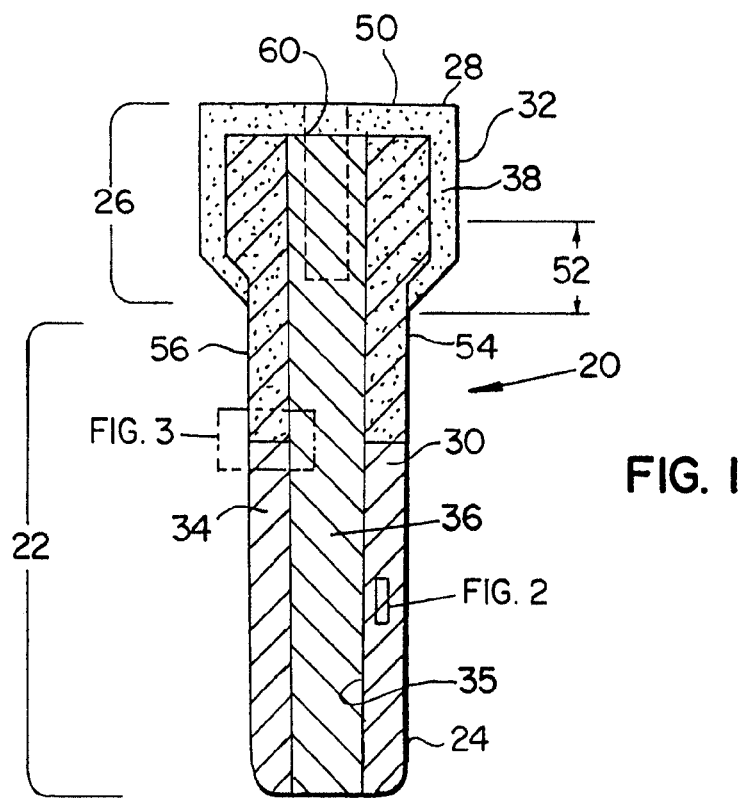
FIG. 1 is a cross-sectional view of a first embodiment of a one-piece dental implant prosthetic device in accordance with the present invention.

Referring to FIG. 1, there is illustrated a pre-fabricated one-piece dental prosthetic device 20. The one-piece dental device 20 has a bone engaging endosseous portion or implant portion 22 on a distal or apical end portion 24 of the device 20 to extend into the maxillae or mandible (either being otherwise generally referred to as the jaw bone). The implant portion 22 supports an abutment portion 26 integrally formed with the implant portion 22 and disposed at a proximal or coronal end portion 28 of the one-piece dental device 20. The abutment portion 26 may include an abutment, an integrally formed dental restoration (i.e., a (near) net-shape tooth or crown), and/or the transmucosal portion of a single stage dental implant. In the form shown in FIG. 1, the abutment portion 26 extends through and above the gingival tissue to support and receive a tooth shaped prosthetic or other types of prosthetic pieces or devices. The one piece dental device 20 also has a porous metal portion or matrix 30 to improve the osseointegration of the bone on at least the implant portion 22. Further, the one piece dental device 20 may have an outer portion 32 that has a color generally replicating the color of natural teeth so that if the abutment portion 26 is still exposed after a prosthetic is placed on the abutment portion, it will still have an aesthetic appearance in a person's mouth. The one-piece dental prosthetic device disclosed herein may also have other geometries, such as those found in U.S. patent application Ser. No. 11/380,569, which is incorporated herein by reference. These features are explained in detail below.

As mentioned, the porous metal portion 30 extends on the implant portion 22 where it can be placed in contact with the bone, and in one form, is a porous tantalum portion 40 which is a highly porous biomaterial useful as a bone substitute and/or cell and tissue receptive material. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is fully incorporated herein by reference. Other metals such as niobium, or alloys of tantalum and niobium with one another or with other metals may also be used.

Figure 2:
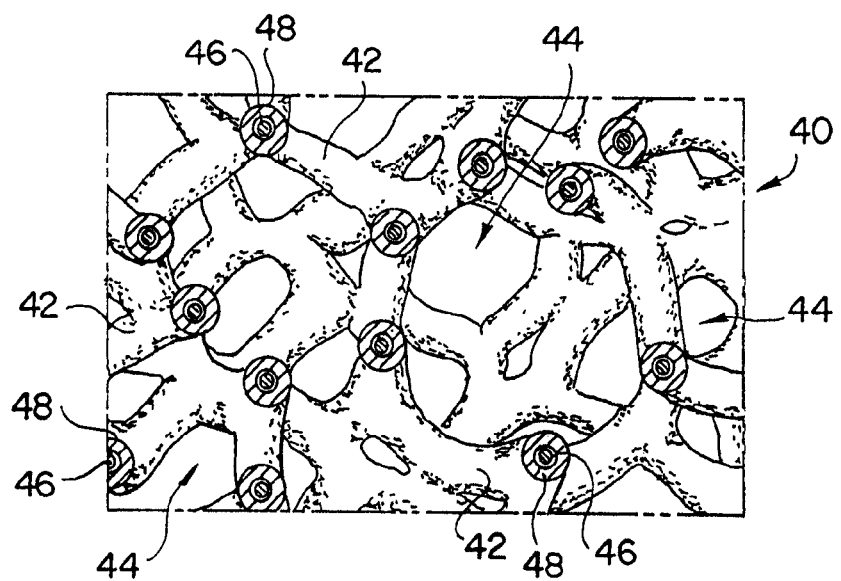
FIG. 2 is an enlarged fragmentary view of a porous tantalum portion for any of the embodiments herein and in accordance with the present invention.

Generally, as shown in FIG. 2, the porous tantalum structure 40 includes a large plurality of ligaments 42 defining open spaces 44 therebetween, with each ligament 42 generally including a carbon core 46 covered by a thin film of metal 48 such as tantalum, for example. The open spaces or pores 44 between ligaments 42 form a matrix of continuous channels having substantially no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor dental device 20 into the surrounding bone of a patient's jaw.

The porous tantalum structure 40 may be made in a variety of densities in order to selectively tailor the structure for particular applications. In particular, as discussed in the above-incorporated U.S. Pat. No. 5,282,861, the porous tantalum may be fabricated to many different desired porosity and pore sizes, and can thus be matched with the surrounding natural bone in order to provide an improved matrix for bone in-growth and mineralization. This includes a gradation of pore size on a single implant such that pores are larger on an apical end to match cancellous bone and smaller on a coronal end to match cortical bone, or even to receive soft tissue in growth. Also, the porous tantalum could be made denser with fewer pores in areas of high mechanical stress. Instead of smaller pores in the tantalum, this can also be accomplished by filling all or some of the pores with a solid material which is described in further detail below.

To provide the additional initial mechanical strength and stability to the porous structure, the porous structure may be infiltrated with filler material such as a non-resorbable polymer or a resorbable polymer. Examples of non-resorbable polymers for infiltration of the porous structure may include a polyaryl ether ketone (PAEK) such as polyether ketone (PEKK), polyether ether ketone (PEEK), polyether ketone ether ketone (PEKEKK), polymethylacrylate (PMMA), polyetherimide, polysulfone, and polyphenolsulfone.

Examples of resorbable polymers may include PLA, PGA, PLGA, PHB, PHV, and copolymers thereof, polycaprolactone, polyanhydrides, and polyorthoesters. By providing additional initial mechanical strength and stability with a resorbable filler material, a titanium reinforcing implant core may not be required. The resorbable material would resorb titanium as the bone grows in and replaces it, which maintains the strength and stability of the implant.

Referring to FIG. 1, the porous metal portion 30 forms a sleeve 34 that at least partially surrounds a core 36. The sleeve 34, core 36, or both as shown may form a strong, reinforcing post that extends into the abutment portion 26 to reinforce the abutment. Here, the sleeve 34 substantially entirely encapsulates the core 36 although many other configurations are possible where the porous metal portion 30 covers only a part of the length or circumference of the core 36 whether continuously or spaced at intervals.

The core 36 is made of a suitable biocompatible material, such as titanium although the core 36 may also be made of other biocompatible materials such as at least one of the following: titanium alloy, stainless steel, zirconium, and cobalt-chromium-molybdenum alloy to name a few examples. The core 36 can be inserted into the sleeve 34 by various known methods such as press-fitting, diffusion bonding, or mechanical threading of the core 36 into the porous metal sleeve 34. Where the core 36 is press-fit into the sleeve 34, a fastening between the two parts is achieved by friction after the two parts are pushed together. The friction that holds the parts together is often greatly increased by compression of one part against the other, which relies on the tensile and compressive strengths of the materials of the engaged parts.

Diffusion-bonding of the core 36 and sleeve 34 is a solid-state joining process that involves holding components under load at an elevated temperature. The process is dependent upon a number of different parameters, such as time, applied pressure, bonding temperature and method of heat application. Alternatively, mechanically threading the core 36 into the sleeve 34 involves providing the sleeve with a threaded bore formed at its interior 35 which mates with a threaded male portion of the core 36. Direct Chemical Vapor Deposition (CVD) bonding can also be used to bond the core 36 with the sleeve 34. This process, like diffusion bonding, is dependent upon a number of different parameters and involves bonding the core 36 and sleeve 34 by depositing a material, such as tantalum, onto the assembly at an elevated temperature.

The one-piece device 20 also may have an esthetic material (also referred to herein as an esthetic portion) 38 that has a color generally replicating the color of natural teeth. In this case, if the outer portion 32 has the esthetic portion 38 and is disposed on the abutment portion 26, for example, and the outer portion 32 is exposed even when a temporary or final prosthesis is placed on the abutment portion 26, the exposed outer portion 32 will still provide an esthetically pleasing appearance.

The esthetic portion 38 may comprise either a polymer, a composite material as disclosed in detail in commonly owned U.S. patent application Ser. Nos. 11/420,024 and 11/622,171, which are fully incorporated herein as mentioned above, or a ceramic material. When the esthetic portion 38 comprises composite materials it may include the combination of a matrix material, a reinforcing material and a colorant. The matrix material may be a polyaryl ether ketone (PAEK) such as polyether Ketone Ketone (PEKK), polyether ether ketone (PEEK), polyether ketone ether ketone ketone (PEKEKK), polymethylmethacrylate (PMMA), polyetherimide, polysulfone, and polyphenylsulfone. The polymers can also be a thermoset material including, without limitation, bisphenol glycidyl methacrylate (Bis-GMA), urethane dimethacrylate (UDMA), methylmethacrylate (MMA), triethylene glycol dimethacrylate (TEGDMA), a combination of thermoset plastics, or a combination of thermoset and thermoplastics. Additionally, they can be comprised of, without limitation, a large class of monomers, oligomers and polymers, such as acrylics, styrenics and other vinyls, epoxies, urethanes, polyesters, polycarbonates, polyamides, radiopaque polymers and biomaterials.

The reinforcing material may comprise, to name a few possible examples, at least one selected from the group comprising carbon, $Al_2O_3$, $ZrO_2$, $Y_2O_3$, $Y_2O_3$-stabilized $ZrO_2$, MgO-stabilized $ZrO_2$, E-glass, S-glass, bioactive glasses, bioactive glass ceramics, calcium phosphate, hydroxyapatite, $TiO_2$, Ti, Ti6Al4V, stainless steel, polyaryl ether ketones (PAEK) such as polyethyl ethyl ketone (PEEK), polyethyl ketone ketone (PEKK), and an aramid. The geometry of the reinforcing material may include fibers, particulates, variable diameter fibers and fibers fused with particulates on the fiber surfaces. The colorant may be titanium dioxide as one example.

In one example, the esthetic portion 38 may comprise about 55% by weight of the composite material PEKK as the matrix material, about 35% by weight of the composite material of E-glass fibers as the reinforcing material, and about 10% by weight of the composite material of titanium dioxide particles as the colorant. In another example, the esthetic portion 38 may comprise about 53% by weight of the composite material PEKK as the matrix material, about 35% by weight of the composite material of E-glass fibers as the reinforcing material, and about 12% by weight of the composite material of titanium dioxide particles as the colorant.

In one form, the outer portion 32 has an exterior separate from the porous tantalum portion so that the outer portion is substantially free of the porous tantalum portion. This results in the exterior of the outer portion 32 forming a smooth skin layer comprised substantially of the esthetic material, where the skin layer of esthetic material may have a thickness of approximately 0.05 to about 3.0 mm. Furthermore, the smooth skin layer of the outer portion 32, when placed along the implant portion 22 or within the transmucosal layer 52 (i.e., gingival region of the prosthetic) on the abutment portion 26, forms a relatively solid, pore-free outer layer. This limits attachment of soft tissue and bacteria onto the outer portion 32 and limits the in-growth of the epithelium so that it does not interfere with bone growth against the implant portion 22. The outer portion 32 may be disposed on at least one of a coronal end of the coronal end portion 28, a side of the coronal end portion 28, and the transmucosal layer 52 on the abutment portion 26, but preferably on substantially all three areas. Thus, a smooth, non-porous outer portion 32 may be provided from the upper end 50 on the abutment portion 26, along the transmucosal region 52 of the abutment portion, and in one case, down to the point where the abutment portion 26 narrows and ends and the implant portion 22 begins. In another form, as shown, a smooth surface 54 may also be provided on the coronal end 56 of the implant portion 22 if desired.

Figure 3:
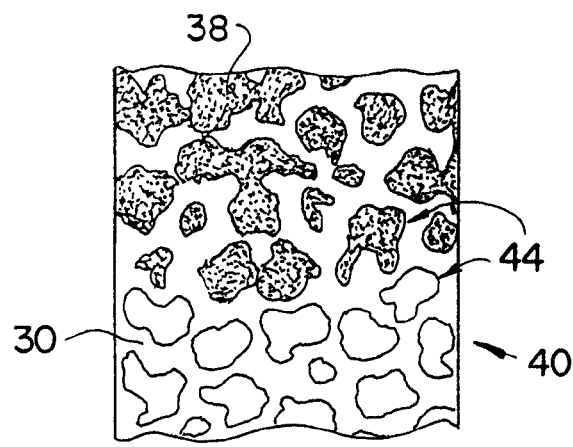
FIG. 3 is an enlarged sectional view of a porous tantalum portion and a filler material for a number of embodiments herein and in accordance with the present invention.

Referring to FIGS. 1 and 3, in another form, the esthetic portion 38 may at least partially impregnate the porous metal portion 30 so that the esthetic portion acts as a filler material and/or the porous metal portion 30 reinforces the esthetic portion 38. In such cases, the esthetic portion 38 fills at least a portion of the pores 44 of the porous metal portion 30. In one form, the esthetic portion 38 substantially completely fills the pores 44 near the coronal end 56 of the implant portion 22 and forms the smooth exterior skin layer 54 mentioned above. The pores 44 of the porous metal portion 30 near the distal end or apical end 24 of the implant portion 22 are substantially free of the esthetic material 38, which allows in-growth of bone to anchor the one-piece dental device 20 to the jaw. Accordingly, there can be a general, internal dividing line above which the porous tantalum is substantially impregnated with esthetic material and below which it is not, similar to the diagram in FIG. 3, and applicable to any of the dental implant devices described herein.

To impregnate the porous metal portion 30 with the esthetic portion 38, the polymers or composites that make up the esthetic material can be injection-molded into the porous metal portion 30 such as on the sleeve 34, so that the polymer or composite material infiltrates the vacant open spaces 44 forming a solid mass of the polymer or composite material with metal reinforcement. Furthermore, injection-molding of the polymer or composite material may also be used to form the non-porous skin layer with the outer portion 32 as described above.

The esthetic portion 38 can also be reinforced by the porous metal portion 30 by an insert-molding process. Insert molding is an injection molding process whereby the esthetic portion 38 is injected into a cavity and around an insert piece, such as the sleeve 34 of porous tantalum, placed into the same cavity just prior to molding, resulting in a single piece with the insert encapsulated by the esthetic portion 38. The impregnation of the porous tantalum portion 30 as shown in FIG. 3 was performed by insert-molding. Other molding processes such as compression molding, resin transfer molding or any other process known in the art may be employed.

Mechanical bonding also takes place during the insert molding process. Mechanical bonding can occur by shrinking of the esthetic portion 38 around the sleeve 34 as the esthetic portion cools or by filling in irregularities in the surface of the sleeve 34. Mechanical bonding further can occur when the esthetic material 38 infiltrates the open spaces within the pores 44 of the porous sleeve 34.

When the esthetic portion 38 is composed of a ceramic material, such as dental porcelain, the ceramic material can be placed in the porous metal portion 30 via sintering and an enameling process. The enameling process includes fusing powdered glass to the porous metal portion 30 by firing at extremely high temperatures. The ceramic powder can melt and flow, and hardens into a smooth, durable ceramic coating that can be placed on the porous tantalum portion and can be inlaid within the pores 44 of the porous tantalum portion. The ceramic material, after firing and cooling, becomes a smooth, hard and very durable material.

A microscopic model can be obtained to predict the overall mechanical properties of the porous metal/composite material-filled structure. For instance, a relationship between the strength of the porous metal/composite material and the strength of a particular filler material (shown in FIG. 11) can be obtained by using a finite element model (as shown in FIG. 12). More specifically, the prediction of the porous metal/composite material structure's overall mechanical behavior can be based on Representative Volume Element (RVE) theory. The RVE theory comprises constructing a representative portion of the material's microstructure (an "RVE") and subjecting it to virtual testing. The overall mechanical behavior of the RVE is found to be equivalent to the composite material it represents.

As an example, an RVE program such as commercially available FE software, ANSYS version 10 (available from ANSYS, Inc., Canonsburg, Pa., USA) is used to generate a two-dimensional stochastic Voronoi cell structure based on RVE theory to simulate random microscopic struts of the porous metal at the microscopic level. Specifically, the porous metal/composite material structure was meshed using 8-node hexagon mesh. The porous metal structure was simulated using tantalum metal material properties as a bi-linear, elasto-plastic material (i.e., having Young's Modulus E=179 GPa, Poisson's ratio μ=0.34, Yield stress σy=190 MPa and Tangent Modulus Et=17 GPa). The pores between the struts were modeled to be impregnated with a composite material as a filler material similar to that shown in FIG. 3 except all pores were filled for the test. The filler composite material was modeled as a linear elastic material having a varied elastic modulus and Poisson's ratio equal to 0.4.

To compute the overall Young's modulus (E) of the structure, a boundary condition was applied to the finite element model as shown in FIG. 12 to simulate compression testing. The finite element model has a fixed, constrained face with an area (Axx) formed by a length in the x direction (Dx) and a length in the y direction (Dy). All other faces are unconstrained along the x-direction. The boundary or test condition used was to apply a uniform strain field with 0.1% strain along the x-direction to the RVE and the finite element model. For instance, in order to compute Exx (Young's modulus along the x-direction), a displacement Ux represents an applied strain where Ux=0.001 Dx. Therefore, Exx can be computed as follows:

$$E_{xx} = 1000 \times \frac{\sum R_x}{A_{xx}}$$

where $\Sigma R_x$ represents the summation of reaction forces at the constrained faces. Due to its structural symmetry, the Young's modulus along the x, y and z directions is the same. Therefore, $E=E_{xx}=E_{yy}=E_{zz}$.

Figure 11:
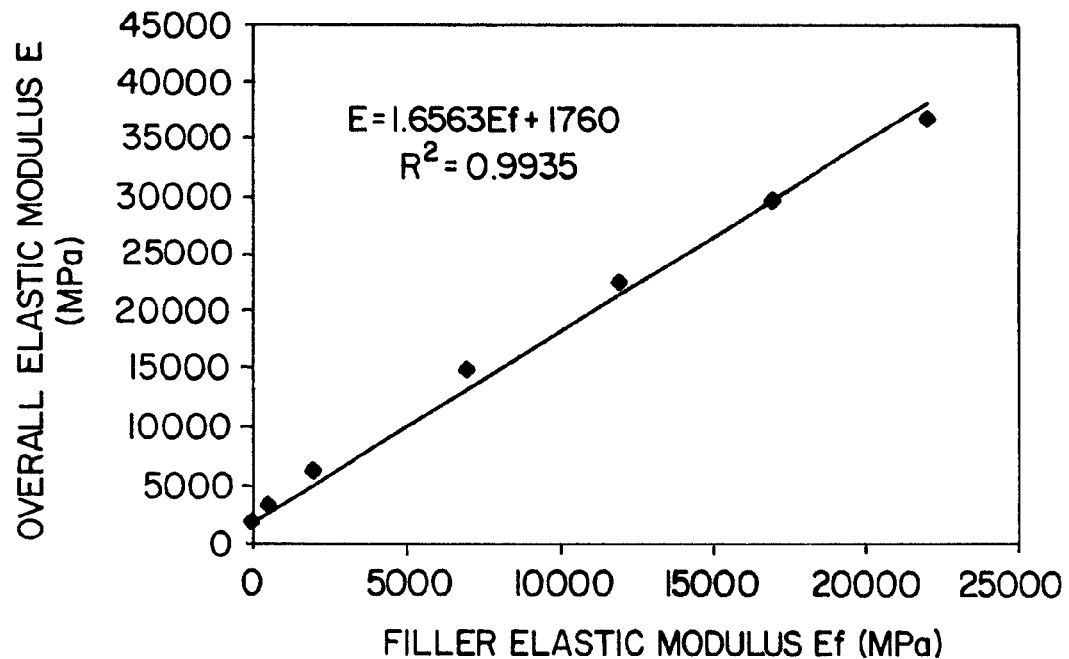
FIG. 11 is a graphical representation of the overall elastic modulus for a porous metal/composite material structure as a function of an elastic modulus of a filler material for the structure.
Figure 12:
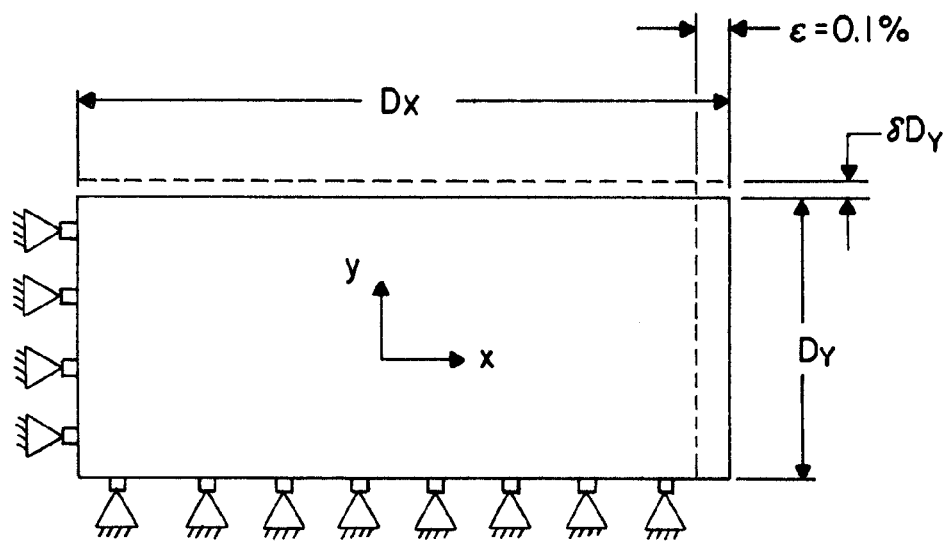
FIG. 12 is a schematic diagram showing the boundary conditions used for computing Young's modulus for the porous metal/composite material structure shown graphically in FIG. 11.

As a result, the overall elastic modulus, E, of the porous metal impregnated with the composite material was plotted versus the filler (i.e., composite material) elastic modulus, Ef, and is shown in FIG. 11. A linear regression was used to fit the data points and an equation was obtained expressing the overall elastic modulus, E, for the porous metal/composite material structure as a function of the filler elastic modulus, Ef, or $E=1760+1.6563E_f$, and further having an R-squared value of 0.9935, where R-squared is a statistical measure of the fraction of variance expressed by the model.

In another form, the one-piece dental device 20, as well as the other implants described below, may have multiple textured surfaces as described in detail in U.S. Pat. No. 5,989,027, assigned to the assignee of the present invention, the disclosure of which is expressly incorporated herein by reference. For example, the sleeve 34 of porous tantalum may have an increasing porosity from the proximal end 28 toward the distal end 24 of the one-piece dental device 20. Thus, the sleeve 34 may be formed of substantially solid, non-porous tantalum near the proximal end 28, within the transmucosal region 52 on the abutment portion 26, and/or slightly distally of the abutment portion 26 to provide a seal with the surrounding gingiva such that plaque or bacteria cannot lodge on or deposit within the sleeve 34 near the gumline of the patient should the upper portion of the sleeve 34 be exposed to the oral cavity. Alternatively, the surface of the abutment portion 26 of the core 36 could be formed of smooth, polished titanium or other materials providing such a smooth, solid finish to allow ready removal of bacterial plaque deposits by conventional oral hygiene techniques. As another option, bands of titanium or other materials may be provided with a solid yet roughened surface, such as at the coronal end 56 of the implant portion 22 to promote some bone growth while still limiting at least some soft-tissue and bacterial growth.

In addition to these approaches, the porosity of the porous metal portion 30 of the sleeve 34 can increase gradually or at intervals as desired and as the sleeve 34 extends distally to promote maximum bone in-growth and osseointegration at the distal end portion 24 of the one-piece dental device 20. For this purpose, the pores 44 of the porous metal structure 30 may be formed with increasingly larger sizes from the proximal end portion 28 to the distal end portion 24 of the one-piece dental device 20.

Also, the sleeve 34 may be attached to the core 36 of the one-piece dental device 20 in a manner wherein, after osseointegration of the sleeve 34 into the surrounding bone, the core 36 is slightly movable relative to the sleeve 34 in order to dissipate forces which are imposed upon the one-piece dental device 20, such as mastication forces, for example. In one embodiment, the sleeve 34 may be secured to the core 36 via an adhesive or cement material which is slightly compressible, such that when mastication or other forces are imposed upon the abutment portion 26, the core 36 may move slightly relative to the sleeve 34 whether within the abutment portion 26 or within the implant portion 22. Such adhesive or cement materials include acid-base reaction formulations such as zinc phosphate, zinc oxide/eugenol, zinc polycarboxylate, glass ionomer, or resin based formulations similar to that of resin-based dental restorative filling materials. One specific example is a dental adhesive/bonding agent that is composed of monomers of hydroxyethyl methacrylate (HEMA), 4-methacryloxyethyl trimellitate anhydride (4-META) and an organophosphate (e.g., 10-methacryloyoxydecamethylene phosphoric acid, MDP). In other embodiments, a compression ring, a spring, or another type of "shock absorbing" structure may be fitted between the core 36 and the sleeve 34 to allow for relative movement therebetween.

Figure 4:
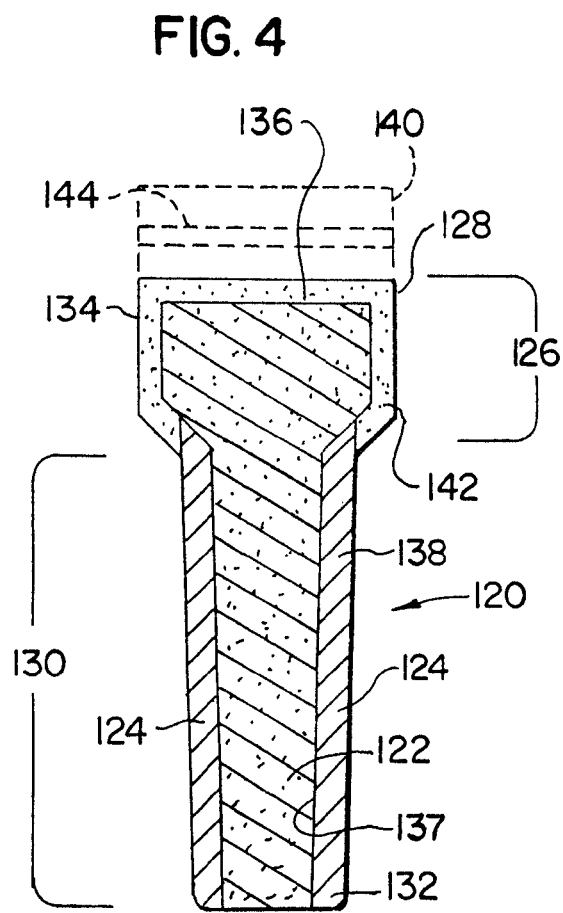
FIG. 4 is a cross-sectional view of a second embodiment of a one-piece dental implant prosthetic device in accordance with the present invention.

Referring to FIG. 4, there is illustrated a one-piece dental device 120 that similarly includes a core 122 and a porous metal portion 124 in the form of a sleeve 138 that at least partially surrounds the core 122 and may be made of a porous tantalum such as Trabecular Metal™. The dental device 120 also has an abutment portion 126 at a proximal end portion 128 of the one-piece dental device 120 and an implant portion 130 at a distal end portion 132 of the one-piece dental device 120. An outer portion 134 having an esthetic material 142, similar to esthetic material 38, has a color generally replicating the color of natural teeth and is disposed at least at the abutment portion 126 of the device 120 as described further below.

For the one-piece dental device 120, the core 122 also is made of a porous metal such as tantalum and may be received by an interior or bore 137 of the sleeve 138. The core 122 can be inserted into the sleeve 138 by various methods such as press-fit or mechanical threading as described above. Alternatively, the sleeve 138 may be integrally formed with the core 122. While the porous metal portion 124 generally remains on the implant portion 130 (i.e. it does not extend substantially onto the abutment portion 126 in this example), the porous metal core 122, in one form, widens and forms the bulk of the abutment portion 126 and forms a strong, reinforcing post that extends from within the implant portion 130 to within the abutment portion 126. Thus, in this case, the porous metal, and therefore, the porous metal portion 134, may be described as generally extending throughout the prosthetic device 120.

For the dental device 120, the core 122 is impregnated with a filler while the porous metal portion 124 forming the sleeve 138 and that forms the exterior of the implant portion 130 for engaging bone is substantially free of the esthetic material. The filler may be a composite or polymer material, which may be the same as the esthetic material 142, and may fill in the vacant open spaces in the porous tantalum as previously discussed above with the embodiment of FIG. 1 and as shown in FIG. 3, except that here, the composite or polymer material fills the pores of the entire length of the core 122 from the proximal end portion 128 to the distal end portion 132. The core 122 may be impregnated by any of the previously discussed methods, such as by injection-molding.

The esthetic material or esthetic portion 142 of the one-piece dental device 120, as mentioned above for the dental device 20, may be disposed at least the outer portion 134 at the abutment portion 126 for esthetics and to at least partially cover the porous tantalum portion of the core 122 at the proximal portion 128 to limit gingival tissue growth there. Thus, at the proximal end portion 128 of the core 122, the outer portion 134 forms a smooth esthetic skin layer that is substantially free of porous tantalum, and is located around substantially the entire abutment portion 126. The outer portion 134 may have a skin layer that is approximately 0.05 to about 3.0 mm thick. With this configuration, the porous sleeve 138 substantially covers the implant portion 130 of the outer layer of the implant 120 to promote bone growth while the exposed abutment portion 126 with a solid, smooth esthetic outer surface limits the in-growth of soft tissue and bacterial growth against the abutment portion 126.

In one variation of the one-piece dental device 120, a thickened, outer and upper portion or layer 140 is formed coronally of the core 122 at the coronal end portion 128 and is made of the esthetic material. The upper layer 140 can be formed by injecting the esthetic material onto the porous structure of the tantalum core 122 until a coronal or terminal end 136 of the core 122 is coated with several millimeters of esthetic material. The layer 140 is substantially free of porous metal so that it can be easily shaped by a practitioner for receiving another dental device or restoration such as a dental prosthesis or final crown, for example.

In another alternative, one or more gaps 144 within the upper layer 140 encourages soft tissue in-growth to form a seal around the perimeter of the implant 120 at the location of the gap 144. This seal coupled with the non-porous outer surface formed by the esthetic portion 142 on the abutment portion 126 forms a barrier that limits bacteria, epithelium or other contaminants from passing through the porous metal and into a bone integration area along the implant portion 130. While the gap 144 is shown as a continuous gap around the upper layer 140 it will be appreciated that many other forms are possible, such as non-continuous gaps, spaced holes, or other uniform or more randomly placed openings, to name a few examples.

Figure 5:
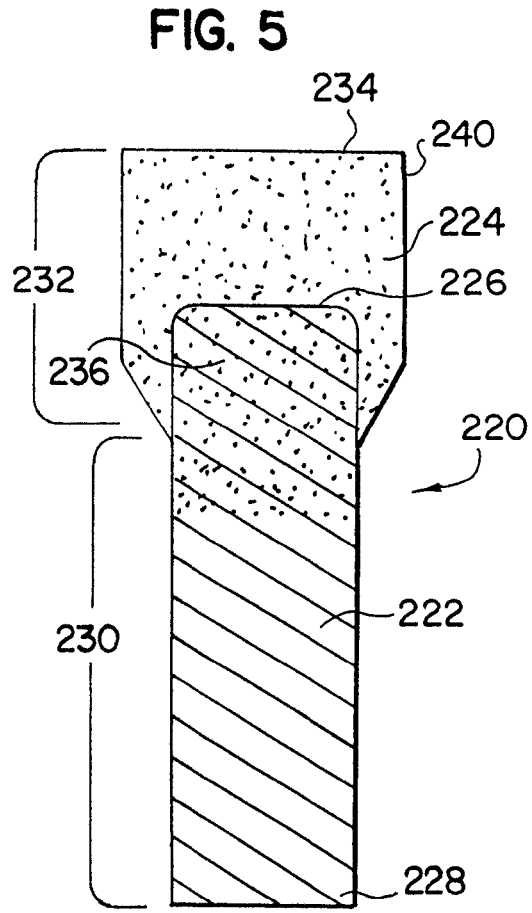
FIG. 5 is a cross-sectional view of a third embodiment of a one-piece dental implant prosthetic device in accordance with the present invention.

Referring to FIG. 5, there is illustrated a third embodiment of a one-piece dental device 220 including a porous metal portion 222 of tantalum or other materials as described above, and an outer portion 240 having a color generally replicating the color of natural teeth and formed by an esthetic portion or material 224 on an abutment portion 232. The porous tantalum portion 222 forms an implant portion 230 at a distal or apical end portion 228 of the dental device 220. The porous metal portion 222 also forms a reinforcing core 236 of the abutment portion 232 at the coronal end portion 234 of the dental device 220. While the core 236 is shown to extend approximately half the height of the abutment portion 232, it will be understood that other variations are possible including the core 236 extending at or near the terminal coronal end 234 of the abutment portion 232 or being much shorter such that the core 236 extends a relatively small distance into the abutment portion 232. In the form illustrated, the core 236 does not extend near the terminal coronal end 234 so that the esthetic portion 224 disposed coronally of the core 236 is separate from the porous metal portion 222 and is substantially free of porous metal so that the end 234 is easily shaped similar to coronal upper layer 140 of dental device 120 (FIG. 4).

In one form, pores are provided generally throughout the porous tantalum portion 222 from a coronal or proximal end 226 of the porous metal portion 222 to the apical end portion 228, and through the implant portion 230. The porous metal portion 222 has pores at least partially impregnated with the esthetic portion 224. The pores at the apical end portion 228 are substantially free of esthetic material while the pores at the coronal end portion 226 are at least partially impregnated with the esthetic material. In one form of device 220, the pores that are substantially free of esthetic material form the majority of the implant portion 230 although other variations are contemplated.

It will also be appreciated that while the porous metal portion 222 is shown to form substantially the entire implant portion 230, other outer sleeves or layers on the porous metal portion 222, whether presenting a solid and/or porous outer surface, may be provided as with the other alternative embodiments described.

It will further be appreciated that the outer portion 240 may be located on any outer part of the abutment portion 232 and may be substantially free of the porous tantalum portion as with the other embodiments herein. The outer portion 240 may contain a smooth exterior layer that has a minimal width of about 1 mm on the sides of the core 236 and/or may have a substantial thickness of about 1 to about 5 mm above the coronal end 226 of the core 236.

Referring again to FIG. 1, to surgically implant the one-piece dental device 20, or any of the implant devices herein, the one-piece dental device 20 may be fitted into a bore drilled into a patient's jaw bone at an edentulous site. In particular, the one-piece dental device 20 may be impacted or press-fitted into the bore to provide a firm initial seating of the one-piece dental device 20 into the bore. For this purpose, the dental device 20 may have a tool or driver-engaging structure 60 such as a bore (shown in dashed line) for receiving a driver to insert the dental device 20 into the bone tissue. The bore 60 may use structures, such as an interference fit, for releasably engaging the driver. Thereafter, the bone tissue surrounding the one-piece dental device 20 may osseointegrate into the open spaces 44 of the porous sleeve 34, thereby firmly anchoring the sleeve 34 and the one-piece dental device 20 into the surrounding bone structure. Thereafter, a temporary or permanent prosthesis may be secured to the esthetic portion 38 in a known manner when the esthetic portion 38 includes an abutment.

Referring to FIGS. 6-10, a press-fitting driver 300 may be used to press fit one-piece dental devices such as those described above or other implants such as implants 320 and 340. Thus, while driver 300 is described with the use of implant 320, any of the implant-devices described herein may be used similarly with the driver 300.

When press-fitting a dental device 320, for example, into a bore on the jaw, it may be desirable to make the fit between the surgical site and the press-fit implant very tight so that the dental device 320 can achieve the required degree of stability for immediate or early loading. To achieve the desired tight fit, it may be difficult to press-fit the dental device 320 into the bore by hand pressure alone. Therefore, a driver 300 may be used to apply pressure to properly press-fit the implant into the bore to achieve a tight fit. In contrast to osteotomes, the driver 300 is fastened directly to the dental device 320 or to an implant carrier, rather than to the jaw site. A single drill can be used to create a pilot hole, or bore, in the jaw and the tip 324 of an implant 320 can be placed into the hole. The driver 300 can be attached to the implant 320 on the end 322 that is opposite the apical tip 324 and a proximal portion or handle 310 of the driver 300 can then be struck with a mallet or other driving tool to deliver a greater force to the implant 320 than could be done by hand in order to achieve the tight fit with the hole. The driver 300 may have a bent portion 312 that extends to, and orients, the proximal portion 310. So configured, the proximal portion 310 is oriented in a certain position and direction (i.e., facially of the jaw) so that an object, such as the mallet, other tool, or even a person's hand has convenient access to the proximal portion 310 away from the area directly between the teeth and outside of the mouth where there is more space to maneuver. The coronal end 322 of the implant 320 may be flat to engage the driver 300 or may have a bore similar to bore 60 on the one-piece dental device 20 (FIG. 1) for receiving the driver 300.

Referring to FIGS. 7-10 and 13-23, implant devices also made of porous material as mentioned above are further provided with a shape to increase stability for early and long-term loading as well as to limit unintentional pull out of the implant devices. More specifically, while the implant devices may be generally or substantially cylindrical, in one form, a porous implant device 400 as shown in FIG. 18 has a body 402 that tapers inwardly as it extends from a coronal end portion 404 of the body 402 to an apical end portion 406 of the body 402. With this structure, the implant device 400 is configured to have the coronal end portion 404 with a larger width dimension than the width dimension of the apical end portion 406. This allows the implant device 400 to expand the bone as the body 402 is inserted into a bore that has a diameter smaller than the maximum width of the body 402, which forms an interference fit. Implant 340 (FIG. 7) also is provided with such an optional taper.

This tapered structure also provides a geometry that is closer to the geometry of the natural tooth. Thus, the slope of the taper may be customized to more closely match the slope of the natural tooth being replaced by the implant device 400. It will be understood that any of the forms of the implant device provided herein may have a taper that forms an interference fit.

Referring to FIGS. 7-8, additionally or alternatively, the implant devices may have an outer periphery shaped to restrict rotation of the implant device within a bore in the jaw bone to create a further interference fit. In one form, implant device 340 has a body portion or body 350 that generally defines a central, coronal-apical axis L1. The implant device 340 also has a porous portion 352 at the body 350 as described above. The porous portion 352 also is disposed at a non-circular, outer periphery portion 354 on the body 350. The non-circular outer periphery 354 at least extends generally around the coronal-apical axis L1. Thus, while the non-circular outer periphery 354 is at least partially made of the porous material, it is entirely made of the porous material in the illustrated form.

The non-circular outer periphery portion 354 is shaped to resist a torsional force that is applied to the implant device 340 and about the axis L1 when the device 340 is disposed within a bore in the jaw bone. The non-circular outer periphery portion 354 has at least three distinct face portions 356. In one form, the outer periphery forms a polygonal portion 342 with vertices 344 at the edges of sidewalls 346 (i.e., the face portions 356). The face portions 356 may be made partially or entirely of the porous material or porous tantalum metal that extends along at least one of the face portions 356. With this configuration, the vertices 344 at the edges of face portions 356 penetrate the usually cylindrical or circular sides of a bore in the jaw bone formed by a dental drill.

The implant device 340 may have a coronal end portion 348 on the body 350 that is configured to receive the driving tool 300 that allows press-fit installation of at least a portion of the body 350 into a bore into the jaw bone. The body 350 can be press-fit into a bore in the bone by using the drive tool 300 or by exerting other types of pressure on the coronal end portion 348 of the dental implant 340 until an interference fit is created between the body 350 and the bone. So configured, the non-circular outer periphery 354 can give the implant device 340 additional stability to resist a rotational or torsional force that is applied to the implant device 340 around the coronal-apical axis L1 while the implant device 340 is disposed within a bore in the jaw bone.

While the non-circular portion 354 may be sized and shaped to resist rotation, it should also have a shape that does not create an unmanageable resistance to translating the implant device 340 for vertically inserting the implant 340 into the bore in the bone. Thus, it will also be understood that while the non-circular portion 354 may axially extend the entire length of the implant 340, or any other length that is advantageous for resisting rotation, the longer the non-circular shape along the implant 340, the more difficult it may be to insert the implant 340 into a circular bore.

In another aspect, as shown in FIGS. 9 and 10, the implant device 320 has a non-circular outer periphery 358 forming a polygonal portion 318 that is stopped short of the full axial length of the implant device 320 to provide space for a plurality of (but at least one) radially extending annular teeth 326. The teeth 326 taper outwardly from the coronal-apical axis as the teeth extend coronally. The annular teeth 326 can be configured to securely contact a bone in a bore and to fasten the implant device 320 within the bore. A porous portion 360 may also be disposed partially or entirely on the body portion 358 or the non-circular outer periphery, including the annular teeth 326, in order to increase the friction between the implant device 320 and the bone and provide a more secure interference fit. In this configuration, the annular teeth 326 are placed into contact with the sidewalls of the bore as the implant device is press-fit into the bore to provide greater stability and increased resistance to the pull-out of the implant device 320 from a bore in the bone.

Figure 14:
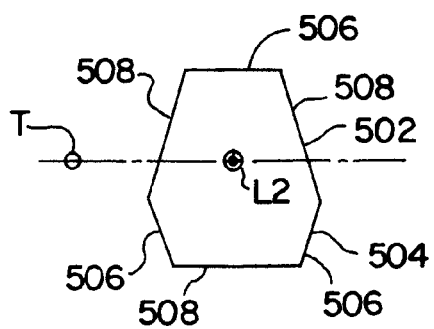
FIG. 14 is a top view of the implant in FIG. 13.
Figure 13:
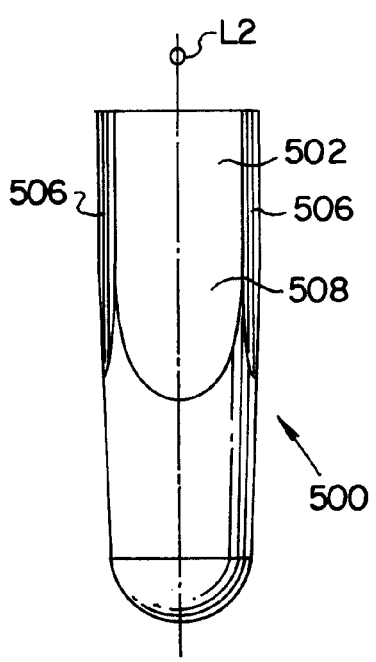
FIG. 13 is a side elevational view of another implant configured for press-fitting in accordance with the present invention.
Figure 15:
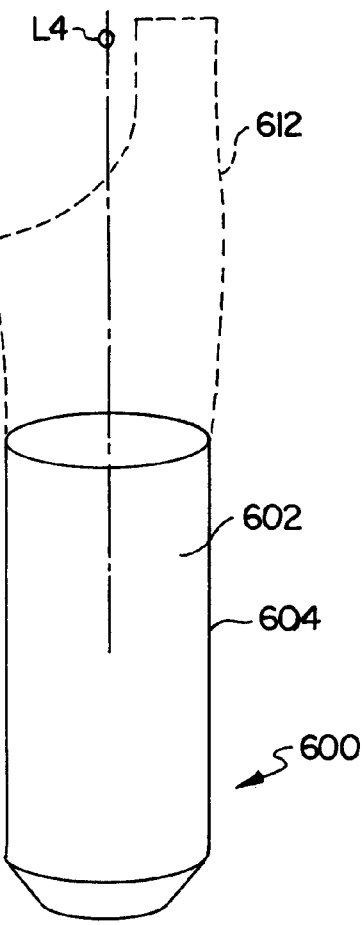
FIG. 15 a side elevational view of another implant configured for press-fitting in accordance with the present invention.
Figure 16:
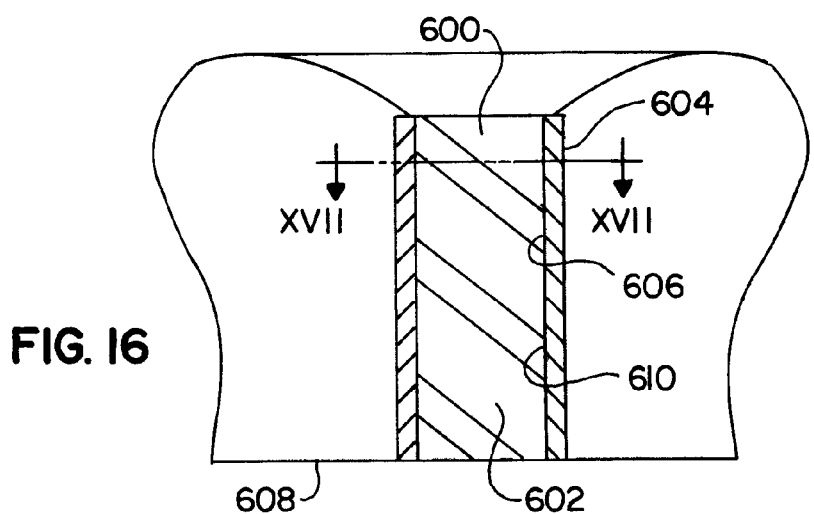
FIG. 16 is a side, cross-sectional view of a bore holding the press-fit implant of FIG. 15 in accordance with the present invention.

Referring to FIGS. 13-14, while the cross-section of the outer periphery in the form of the polygonal portion 318 or 342 is shown to be a regular polygon, alternatively, implant device 500 has an outer periphery 502 that is an irregular polygon or other multi-sided shape with distinct face portions 504 that is asymmetrical about an axis T traverse to the coronal-apical axis L2. In the illustrated form, an irregular hexagon is shown with three small face portions 506 and three wide face portions 508. Otherwise, the structure is that of the implant device 340. It will be understood that many other multi-sided shapes are contemplated.

Referring to FIGS. 15-19, rather than distinct face portions that form flat sides, implant devices 400 and 600 respectively have bodies 402 and 602 with non-circular outer peripheries 408 and 604 that have a closed, curved shape extending around a coronal-apical axis L3 and L4, respectively. For example, outer periphery 604 of implant device 600 is generally oval for fitting tightly into a circular bore in a jaw bone to resist a torsional force applied to the implant device 600 and about axis L4. Tapered implant device 400 is similarly oval (FIGS. 18-19). It will be understood that the non-circular periphery may be any other convexly curved shape such as elliptical or obround. Alternatively, the outer peripheries may have a closed, curved shape that is concavely curved such that a portion on the non-circular outer periphery is shaped to extend inwardly toward the center of the implant device. In another alternative configuration, the non-circular outer periphery may have a number of curves to form a bumped, scalloped, and/or serrated shape. It should also be understood that the non-circular outer periphery could contain a variety of other cross sectional shapes including peripheries that are a combination of flat sides or face portions and curved sections.

Whether or not the non-circular, outer periphery is curved or has distinct sides, the mechanical fixation of the implant device within a bore by interference fit is strengthened by forming the porous material at the outer periphery because the porous material has such a relatively high co-efficient of friction with bone.

To further strengthen the interference fit, the outer periphery may be provided with a maximum width slightly greater than the diameter of the bore in the jaw bone that receives the implant device. So configured, as the implant device is inserted into the bore in a jaw bone, the larger outer periphery roughened by the porous material will bite into the bone by grating, chipping and/or flaking bone pieces off of the sidewalls of the bore in which the implant device is being placed. This "rasping" action forms slight recesses or indents within the bore sidewall in which the implant device sits. This further restricts rotational or twisting motion of the implant device within the bore since the implant device does not have the clearance to rotate out of the indents and within the bore.

The rasping action also accelerates osseointegration onto the implant device and into the pores of the porous material due to the bone compaction into the pores. First, the grating of the bone structure causes the bone to bleed which stimulates bone growth by instigating production of beneficial cells such as osteoblasts and osteoclasts. Second, the bone pieces that fall into the pores on the porous material assist with bone remodeling. In the process of bone remodeling, osteoblast cells use the bone pieces as scaffolding and create new bone material around the bone pieces. Meanwhile osteoclast cells remove the bone pieces through resorption by breaking down bone and releasing minerals, such as calcium, from the bone pieces and back into the blood stream. The osteoblast cells will continue to replace the grated bone pieces from the pores and around the implant device with new and healthy bone within and surrounding the extraction site. Thus, with the porous material, the implant device has increased resistance to twisting or rotation, allows for immediate or very early loading, and increases long-term stability due to the improved osseointegration.

Referring again to FIGS. 15-17, in one specific example, the implant device 600 is disposed within a bore 606 in a jaw bone 608. The non-circular outer periphery 604 may be dimensioned to penetrate the usually cylindrical side 610 of the bore 606 formed by a dental drill. Thus, the maximum width dimension W of the implant device 600 is greater than the diameter D of the bore 606. The difference between W and D (or 2× the interference length 'x'—or 2× as shown on FIG. 17) should not be too small or too large. If the difference is too large (i.e., the maximum implant device width W is much longer than the bore diameter D), the practitioner will not be able to press fit implant device 600 into bore 606 without using a force that could damage the jaw bone or dental implant device 600. If the difference between W and D is too small, the implant device 600 will lack sufficient initial stability and will not grate or scrape a sufficient amount of bone tissue from the bore sidewall 610 to stimulate significant bone growth. In one form, the difference between W and D (or in other words, 2×) should be about 0.008 to 0.18 mm when W is 3.7 mm to 6.0 mm. This corresponds to an interference volume of about 5-20 mm$^3$ where 2× forms the total width of the interference volume as shown on FIG. 17, and the volume extends generally the height of the implant device 600 as shown in dash line on FIG. 16. These dimensions apply to implants having typical axial lengths of about 8 mm to about 16 mm.

It will be understood that implant device 600, as well as any of the other implant devices with anti-rotational features, may have transgingival extensions 612 (shown in dash-line on FIG. 15) including one-piece implants with integral abutments or single-stage surgery implants with an integral emergence profile that attaches to a separate abutment.

It will also be understood that many of the features shown on implants 320, 340, 400, 500, and 600 may be provided for any of the implant devices described herein.

Referring to FIGS. 20-23, another way to restrict rotational movement of an implant device embedded in the jaw bone is to provide the implant device with multiple roots which makes the implant asymmetric at least along the roots. When such a multi-root implant device is placed in a bore in the jaw bone that is shaped to correspond to the shape of the implant device, the roots are each placed in a bore branching off of a main bore. In this case, the dental implant does not have the clearance within the bores to rotate about its coronal-apical axis when a torsional force is applied to the implant device and about its axis.

A multi-root implant may also simplify the surgery when the implant has the same number of roots and general configuration as the natural tooth it is replacing. For instance, the implant may have two or three roots to correspond to the configuration of a molar or pre-molar with the same number of roots. In this case, the bore receiving the multiple-root implant may require minimal drilling to shape the bore when the bore is at the extraction site of the molar or pre-molar being replaced by the implant. This allows the implant device to be immediately placed into the extraction site, preserves more of the natural gum tissue for the patient, and presents a more aesthetic result.

Figure 20:
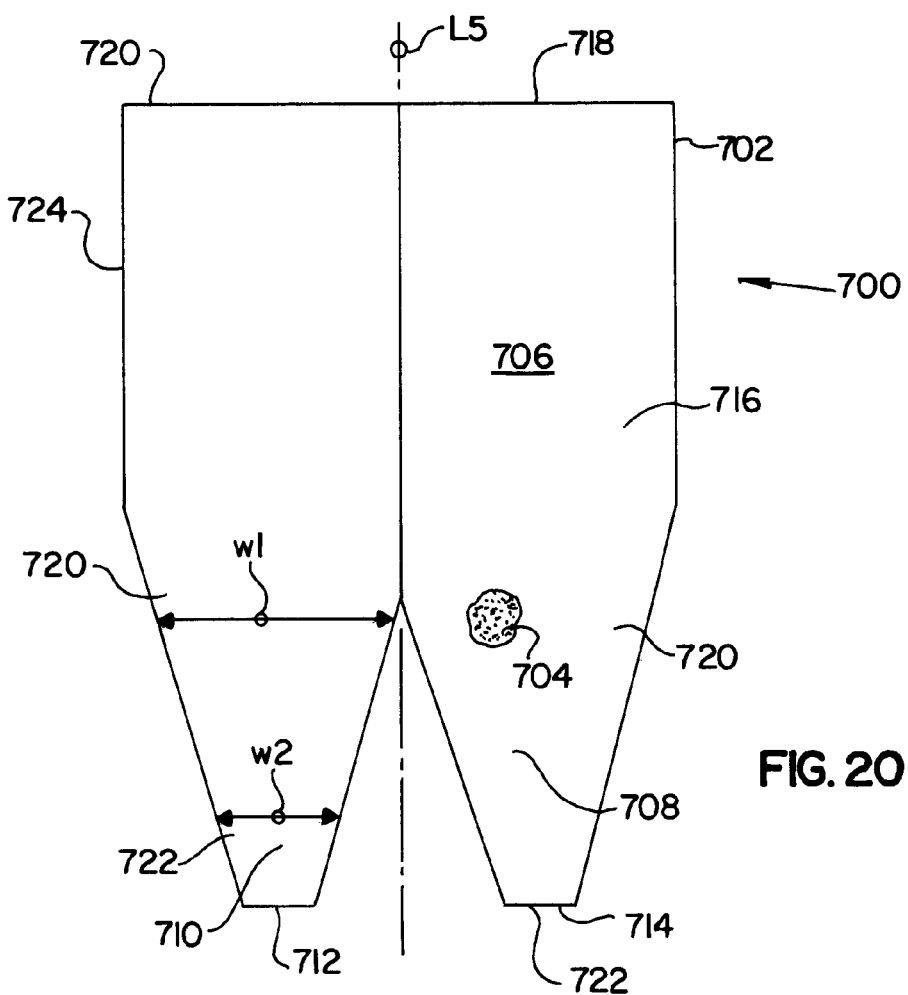
FIG. 20 is a side elevational view of a multiple-root implant in accordance with the present invention.
Figure 21:
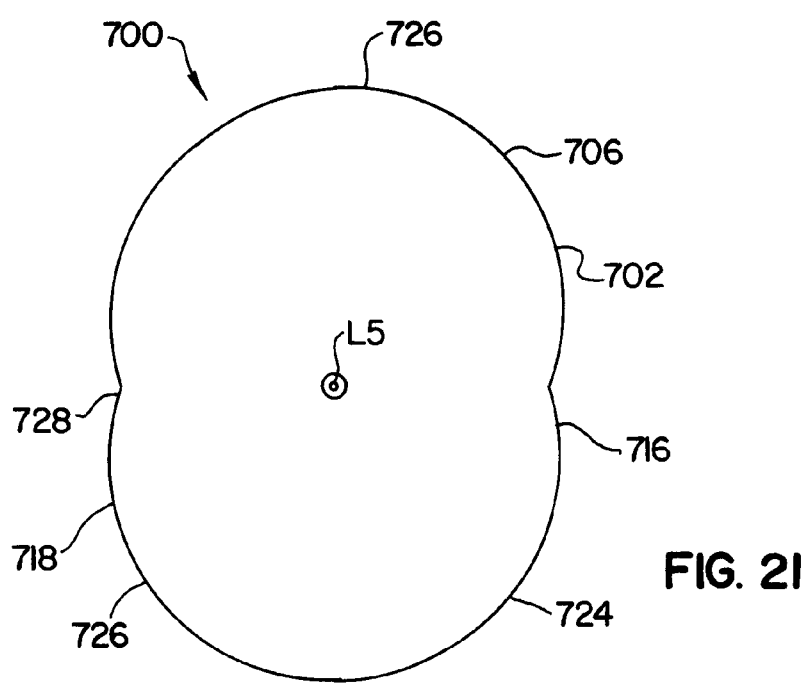
FIG. 21 is a top view of the multiple-root implant of FIG. 20 in accordance with the present invention.

Referring to FIGS. 20-21, in one specific example, a multiple-root implant device 700 has a body 702 that generally defines a coronal-apical axis L5 and a porous portion 704, such as the porous tantalum portion described above, disposed at the body 702. The body 702 has a main portion 706 and roots 708 and 710 extending outwardly from the main portion 706 and to free, distal ends 712 and 714, respectively. The porous portion 704 may form substantially the whole body 702, at least part of one or more roots 708, and 710, and/or at least part of the main portion 706.

The main portion 706 includes an intermediate portion 716 relative to the full coronal-apical length of the implant device 700. The roots 708 and 710 extend or branch out from the intermediate portion 716. The roots 708 and 710 extend in a general apical direction, and in one form generally parallel to the coronal-apical axis L5 of the implant device 700. Implant device 700 is shown with two roots to generally correspond to a natural tooth with two roots such as the mandibular molars or maxillary premolars. It will be understood, therefore, that the roots 708 and 710 could be modified to extend more laterally to match the exact configuration of a particular natural tooth, and in turn, the extraction site to receive the implant device 700. Thus, it will be understood that any of the multiple-root implant devices described herein can be configured such that the multiple roots are arranged and extend in a general direction that corresponds to the arrangement of the roots on the natural tooth that the dental implant replaces.

In one form, at least one of the plurality of distinct roots 708 and 710 can be integrally formed with the main portion 706 but may otherwise be separately formed and connected to the main portion 706.

To insert the multi-root implant device 700 into a bore at an extraction site, the roots should be aligned with the separate branch bores. Pressure is then applied to a coronal tip portion 718 of the implant device 700 and in an insertion direction as explained above for other press-fit implant devices. As the pressure is applied, the plurality of distinct roots 708 and 710 may engage the bone and fasten the implant device 700 into the bore(s) and create an interference fit as well as a mechanical fixation between the implant device 700 and the bone that restricts substantial rotation of the implant device 700 about its coronal-apical axis L5.

As mentioned above, the implant device 700 can have a porous portion disposed on at least one of the plurality of roots 708 and 710 to strengthen the interference fit with the bore. In one alternative, the roots 708 and 710 can be configured to taper inwardly as the roots extend outwardly from the main portion 706. Specifically, the root or roots have a coronal end portion 720 adjacent to the main portion 706 and an apical end portion 722. In this alternative, the coronal end portion 720 has a width dimension w1 greater than the width dimension w2 of the apical end portion 722. Thus, as the implant device 700 is inserted into a bore in the bone, the root will expand the branch bore in which it is inserted, forming a very strong interference fit.

In addition, or in the alternative, at least one of the plurality of distinct roots 708 and/or 710 can have a cross-sectional dimension greater than a corresponding cross-sectional dimension of a branch bore in bone for receiving the root 708 and/or 710 similar to the oversizing provided on the implant devices 320, 340, 400, 500, and 600 described above. So dimensioned, as the implant device 700 is moved in an insertion direction, the porous portion 704 grates pieces of bone off of a sidewall of the branch bore as described above to stimulate bone remodeling and increase initial stability. This dimensioning also can be applied to the main portion 706 as well.

Referring to FIG. 21, the main portion 706 of the multiple-root dental implant device 700 also can include a non-circular outer periphery 724 to restrict rotation of the implant device 700 within a bore as previously described above for the other forms of the implant device. In this case, the non-circular outer periphery 724 extends about the coronal-apical axis and may have a plurality of convexly curved portions 726 where each curved portion 726 coronally aligns with a different one of the plurality of roots 708 or 710. This forms an elongated indent or groove 728 at the intersection of adjacent curved portions 726 and provides the non-circular out periphery with an asymmetric cross-section to resist rotation (where asymmetric means asymmetric about an axis transverse to the apical-coronal axis L5). It will be understood that the roots 708 and 710 could also have any of the non-circular outer peripheries described above.

Figure 22:
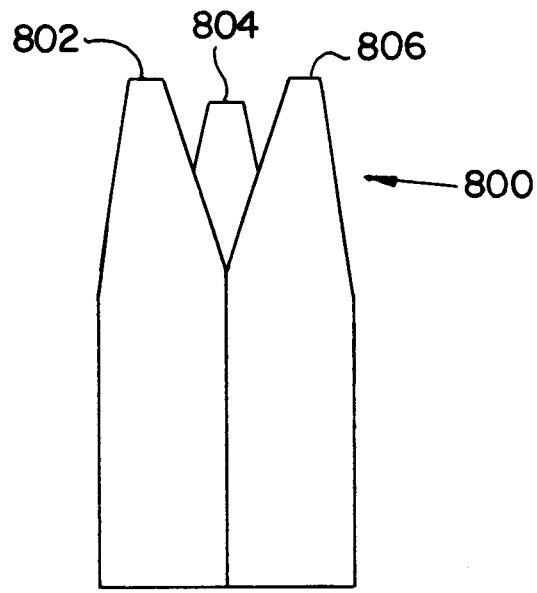
FIG. 22 is a side elevational view of a three-root implant in accordance with the present invention.

Referring briefly to FIG. 22, a three root dental implant device 800 has three distinct roots 802, 804, and 806 but is otherwise the same or similar to implant device 700. Implant device 800 is particularly useful for replacing natural maxillary first, second, or third molars with three roots or a single or double root tooth that may have grown an extra supernumerary root.

Figure 23:
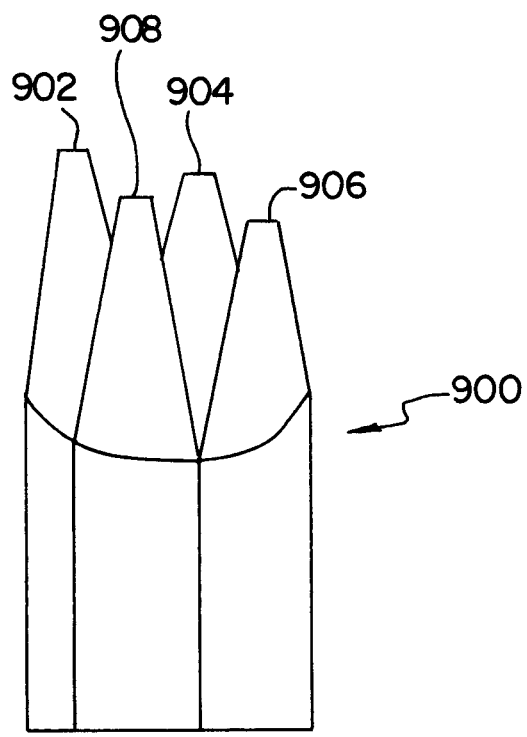
FIG. 23 is a side, perspective view of a four-root implant in accordance with the present invention.

Referring to FIG. 23, a dental implant device 900 can have three or more roots. In this case, a four root implant device 900 is shown. The structure of the implant device 900 is similar or the same as to that described above for the other multi-root implant devices except that here implant device 900 has roots 902, 904, 906, and 908. A dental device 900 may provide more than the normal number of roots to correspond to natural teeth with supernumerary roots. Oftentimes, this condition occurs in mandibular canines, premolars, and maxillary molars, and especially third molars. Thus, the multi-root dental implant devices may match the number of roots no matter what that number or configuration is on the natural tooth, and in turn, at the extraction site. It also will be appreciated that more than the usual number of roots may be used when such structure is deemed beneficial for anchoring the tooth in the jaw bone regardless of the number of roots on the natural tooth to be replaced, if the tooth even existed. This may be used when more surface area on the implant device is desired.

While the implant devices 320, 340, 400, 500, 600, 700, 800, and 900 may be substantially made of the porous material, it will be understood that the implant devices may alternatively have a titanium core with a porous sleeve placed around the core. The porous material may be assembled or bonded to the core by diffusion bonding or direct chemical vapor deposition processes. The porous material and core may also be press-fit together. The stress required to disassemble the bonded or press-fit core to porous material interface, if present, should exceed 20 MPa. The non-porous parts of the dental implants may be machined, EDM cut, or made by using net-shape (custom) manufacturing processes.

While the illustrated forms are shown to be dental implants, it will be understood that such structures, with porous metal or porous tantalum portions on an implant with a non-circular periphery or multi-root implant to restrict rotation in a bore, may be applied to implants used on other areas of a human body or animal, whether or not such an implant is to be inserted into bone.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

What is claimed is:

1. A dental implant for replacement of a single natural tooth and insertion into a bore at the extraction site of the single natural tooth, the dental implant comprising:
    a unitary body defining a coronal-apical axis and having a coronal main shaft portion, a plurality of distinct roots extending apically from the main shaft portion to a distal end, and the main shaft portion including a non-circular closed outer periphery to engage bone, the main shaft portion being shaped and sized to substantially conform to a circular bore in a jaw upon insertion into the bore, wherein the roots are integrally formed with and extending apically from the main shaft portion, wherein the closed outer periphery has a plurality of contiguously convexly curved portions interconnected to surround the coronal apical axis with each curved portion coronally aligning with a different one of the plurality of roots, and wherein each pair of adjacent curved portions of the plurality of curved portions intersects to form an elongated indent or groove that extends in a coronal-apical direction on the main portion; and
    a porous tantalum portion disposed at least on the roots at the unitary body for engaging bone.

2. The dental implant of claim 1 wherein the roots are configured to resist a torsional force applied to the implant and about the coronal-apical axis.

3. The dental implant of claim 1 wherein the unitary body comprises a coronal to apical length and an intermediate portion relative to the coronal to apical length, and wherein the roots extend outward from the intermediate portion.

4. The dental implant of claim 1 wherein the plurality of roots generally extend in an apical direction.

5. The dental implant of claim 1 wherein at least one of the plurality of roots tapers inwardly as the root extends outwardly from the main shaft portion.

6. The dental implant of claim 1 wherein the plurality of distinct roots comprises between two and four roots.

7. The dental implant of claim 1 where the dental implant is configured to have the same number of roots as a natural tooth the dental implant replaces.

8. The dental implant of claim 1 wherein at least one of the roots is configured to have a cross-sectional dimension greater than a corresponding cross-sectional dimension of a bore in bone for receiving the root with a friction fit.

9. The dental implant of claim 1 wherein the porous tantalum portion is configured to grate bone pieces off of a sidewall of a bore in bone that receives the dental implant.

10. The dental implant of claim 1 wherein the porous tantalum portion is disposed at the main shaft portion.

11. The dental implant of claim 1 wherein the outer periphery is configured to have a cross-sectional dimension greater than a corresponding cross-sectional dimension of a bore in bone for receiving the implant with a frictional fit.

12. The dental implant of claim 1 wherein the porous tantalum portion is at least partially filled with a resorbable material.

13. An implant for replacement of a single natural tooth and insertion into a bore at the extraction site of the single natural tooth, the implant comprising:
    a unitary body having a main shaft portion configured with a non-circular closed outer periphery for engaging bone and a plurality of distinct roots extending apically from the main shaft portion to a distal end, the main shaft portion being shaped and sized to substantially conform to a circular bore in a jaw upon insertion into the bore, wherein the roots are integrally formed with and extending apically from the main shaft portion;
    a porous tantalum portion disposed at the unitary body for engaging bone within a bore on an animal or human body; and
    wherein the unitary body generally defines a coronal-apical axis, and wherein the main shaft portion comprises a plurality of contiguous convexly curved portions interconnected to surround the coronal apical axis, wherein at least one pair of adjacent convexly curved portions intersect to form an elongated indent or groove that extends in a coronal-apical direction, and wherein the roots are configured to resist a torsional force applied to the implant and about the coronal-apical axis.

14. The implant of claim 13 is a dental implant.

15. The dental implant of claim 1 wherein the unitary body is non-threaded.

16. The implant of claim 13 wherein the unitary body is non-threaded.

17. A dental implant for replacement of a single natural tooth and insertion into a bore at the extraction site of the single natural tooth, the dental implant comprising:
    a unitary, non-threaded body defining a coronal-apical axis and having a coronal main shaft portion, a plurality of distinct roots extending apically from the main shaft portion to a distal end, and the main shaft portion including a non-circular closed outer periphery to engage bone, the main shaft portion being shaped and sized to substantially conform to a circular bore in a jaw upon insertion into the bore, wherein the roots are integrally formed with and extending apically from the main shaft portion, the closed outer periphery has a plurality of contiguously convexly curved portions interconnected to surround the coronal apical axis with each curved portion coronally aligning with a different one of the plurality of roots, and each pair of adjacent curved portions of the plurality of curved portions intersects to form an elongated indent or groove that extends in a coronal-apical direction on the main shaft portion; and
    a porous tantalum portion disposed at least on the roots for engaging bone.

* * * * *

UNITED STATES PATENT AND TRADEMARK OFFICE
CERTIFICATE OF CORRECTION

PATENT NO. : 9,149,345 B2
APPLICATION NO. : 12/167032
DATED : October 6, 2015
INVENTOR(S) : Lomicka et al.

It is certified that error appears in the above-identified patent and that said Letters Patent is hereby corrected as shown below:

In the claims,

In column 18, line 10-32, in Claim 13, delete "13. An implant for replacement of a single natural tooth and insertion into a bore at the extraction site of the single natural tooth, the implant comprising: a unitary body having a main shaft portion configured with a non-circular closed outer periphery for engaging bone and a plurality of distinct roots extending apically from the main shaft portion to a distal end, the main shaft portion being shaped and sized to substantially conform to a circular bore in a jaw upon insertion into the bore, wherein the roots are integrally formed with and extending apically from the main shaft portion; a porous tantalum portion disposed at the unitary body for engaging bone within a bore on an animal or human body; and wherein the unitary body generally defines a coronal-apical axis, and wherein the main shaft portion comprises a plurality of contiguous convexly curved portions interconnected to surround the coronal apical axis, wherein at least one pair of adjacent convexly curved portions intersect to form an elongated indent or groove that extends in a coronal-apical direction, and wherein the roots are configured to resist a torsional force applied to the implant and about the coronal-apical axis." and insert --13. The dental implant of claim 1 wherein the unitary body is non-threaded.--, therefor In column 18, line 33, in Claim 14, delete "14. The implant of claim 13 is a dental implant." and insert --14. An implant for replacement of a single natural tooth and insertion into a bore at the extraction site of the single natural tooth, the implant comprising: a unitary body having a main shaft portion configured with a non-circular closed outer periphery for engaging bone and a plurality of distinct roots extending apically from the main shaft portion to a distal end, the main shaft portion being shaped and sized to substantially conform to a circular bore in a jaw upon insertion into the bore, wherein the roots are integrally formed with and extending apically from the main shaft portion; a porous tantalum portion disposed at the unitary body for engaging bone within a bore on an animal or human body; and Signed and Sealed this
Eighth Day of March, 2016

Michelle K. Lee
*Director of the United States Patent and Trademark Office* wherein the unitary body generally defines a coronal-apical axis, and wherein the main shaft portion comprises a plurality of contiguous convexly curved portions interconnected to surround the coronal apical axis, wherein at least one pair of adjacent convexly curved portions intersect to form an elongated indent or groove that extends in a coronal-apical direction, and wherein the roots are configured to resist a torsional force applied to the implant and about the coronal-apical axis.--, therefor In column 18, line 34-35, in Claim 15, delete "15. The dental implant of claim 1 wherein the unitary body is non-threaded." and insert --15. The implant of claim 14 is a dental implant.--, therefor In column 18, line 36-37, in Claim 16, delete "16. The implant of claim 13 wherein the unitary body is non-threaded." and insert --16. The implant of claim 14 wherein the unitary body is non-threaded.--, therefor